(12) United States Patent
Nakanishi

(10) Patent No.: US 10,449,155 B2
(45) Date of Patent: Oct. 22, 2019

(54) DRUG INTRODUCING AGENT FOR ADMINISTRATION INTO A LIVING BODY AND MANUFACTURING METHOD

(71) Applicant: Medical Corporation Ijunkai, Osaka (JP)

(72) Inventor: Hiroyuki Nakanishi, Osaka (JP)

(73) Assignee: Medical Corporation Ijunkai, Sakai-Shi, Osaka (JP)

( * ) Notice: Subject to any disclaimer, the term of this patent is extended or adjusted under 35 U.S.C. 154(b) by 0 days.

(21) Appl. No.: 15/346,401

(22) Filed: Nov. 8, 2016

(65) Prior Publication Data

US 2017/0128377 A1    May 11, 2017

(30) Foreign Application Priority Data

Nov. 9, 2015  (JP) .................................. 2015-219754
Nov. 7, 2016  (JP) .................................. 2016-217225

(51) Int. Cl.
| | | |
|---|---|---|
| *A61K 9/50* | (2006.01) | |
| *A61K 47/02* | (2006.01) | |
| *A61K 9/14* | (2006.01) | |
| *A61K 9/00* | (2006.01) | |
| *A61K 31/7105* | (2006.01) | |

(52) U.S. Cl.
CPC ............ *A61K 9/501* (2013.01); *A61K 9/0019* (2013.01); *A61K 31/7105* (2013.01); *A61K 47/02* (2013.01); *C12N 2310/141* (2013.01); *C12N 2320/32* (2013.01)

(58) Field of Classification Search
CPC ......... A61L 27/12; A61K 9/501; A61K 47/02; A61K 9/143
See application file for complete search history.

(56) References Cited

U.S. PATENT DOCUMENTS

| | | | | |
|---|---|---|---|---|
| 5,156,623 | A * | 10/1992 | Hakamatsuka ...... | A61K 9/0024 604/890.1 |
| 6,344,209 | B1 * | 2/2002 | Saito ...................... | A61K 47/26 424/426 |
| 2006/0024377 | A1 * | 2/2006 | Ying ...................... | A61K 9/143 424/489 |
| 2007/0077306 | A1 * | 4/2007 | Akaike ................... | C01B 25/32 424/489 |
| 2014/0161886 | A1 * | 6/2014 | Murphy .................. | A61K 9/501 424/490 |
| 2014/0302145 | A1 * | 10/2014 | Yamamoto ............ | A61K 9/0019 424/489 |

FOREIGN PATENT DOCUMENTS

| | | |
|---|---|---|
| JP | 5-255095 A | 10/1993 |
| JP | 2003-500202 A | 1/2003 |
| JP | 2005-075717 A | 3/2005 |
| JP | 2006-509838 A | 3/2006 |
| JP | 2010-524859 A | 7/2010 |
| JP | 2014-105197 A | 6/2014 |
| JP | 2015-89874 A | 5/2015 |
| JP | 2015-155392 A | 8/2015 |
| WO | 2004/043495 A1 | 5/2004 |
| WO | 2008/128123 A1 | 10/2008 |
| WO | 2015/068713 A1 | 5/2015 |
| WO | WO2015/133522 * | 9/2015 ......... A61K 31/7105 |

OTHER PUBLICATIONS

Viscopedia, viscosity table for water, 2008, http://www.viscopedia.com/viscosity-tables/substances/water/ (Year: 2008).*
Chowdhury, pH-sensitive nano-crystals of carbonate apatite for smart and cell-specific transgene delivery, Expert Opin. Drug Deliv., 2007, vol. 4, p. 193-196. (Year: 2007).*
Liu et al. (Diagnostic and prognostic value of plasma microRNA deregulation in nasopharygeal carcinoma, Cancer Biology & Therapy, 2013, vol. 14, pp. 1133-1142) (Year: 2013).*
Murphy et al. (Growth of hydroxyapatite coating on biodegradable polymer microspheres, Applied Materials and Interfaces, 2009, vol. 1, pp. 1504-1511 (Year: 2009).*
Tanaka et al. (Calcium phosphate formation on titanium by low voltage electrolytic treatments, J. Mater Sci: Mater Med., 2007, vol. 18, pp. 797-806) (Year: 2007).*
Hossain et al. (fabrication and intracellular delivery of doxorubicin/carbonate apatite nanocomposites: effects on growth retardation of established colon tumor, PLOS, 2013, vol. 8, e60428, pp. 1-11) (Year: 2013).*
Universal Medical (50 mL centrifuge tube with blue screw caps-polypropylene, 1983, https://www.universalmedicalinc.com/50ml-centrifuge-tubes-with-blue-screw-caps-polypropylene-pp.html) (Year: 1983).*

* cited by examiner

*Primary Examiner* — Bethany P Barham
*Assistant Examiner* — Peter Anthopolos
(74) *Attorney, Agent, or Firm* — Seed IP Law Group LLP

(57) ABSTRACT

The present invention provides carbonate apatites with a suitable particle size (average particle size and maximum particle size) as well as small variance ($\sigma^2$) of particle sizes. Provided is a method of manufacturing a carbonate apatite, the method comprising the step of incubating a mixture comprising a calcium ion, a phosphate ion, and a hydrocarbon ion, wherein an incubation temperature is 10° C. or lower and an incubation time of 10 minutes or less. Further, a carbonate apatite made by this method (e.g., carbonate apatite with a maximum particle size of 700 nm, average particle size of 30 nm and drug encapsulation rate of 98%, all in nanometer size) is provided.

13 Claims, 12 Drawing Sheets
Specification includes a Sequence Listing.

[Fig. 1]
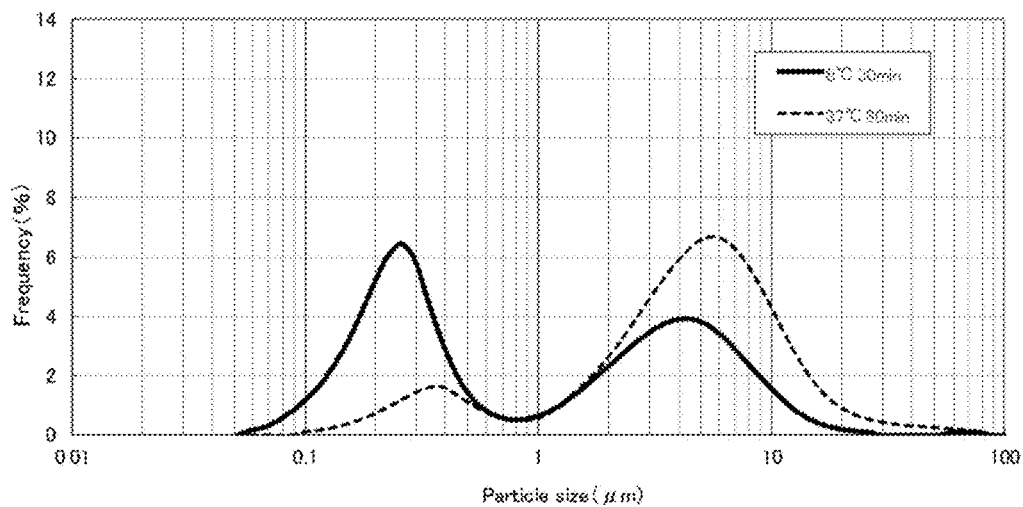
[Fig. 2]
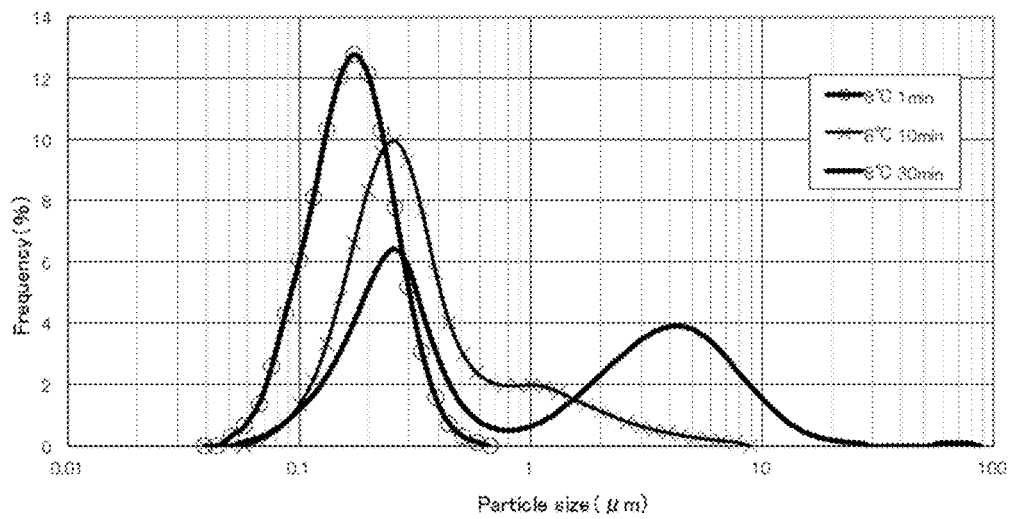

[Fig. 3A]
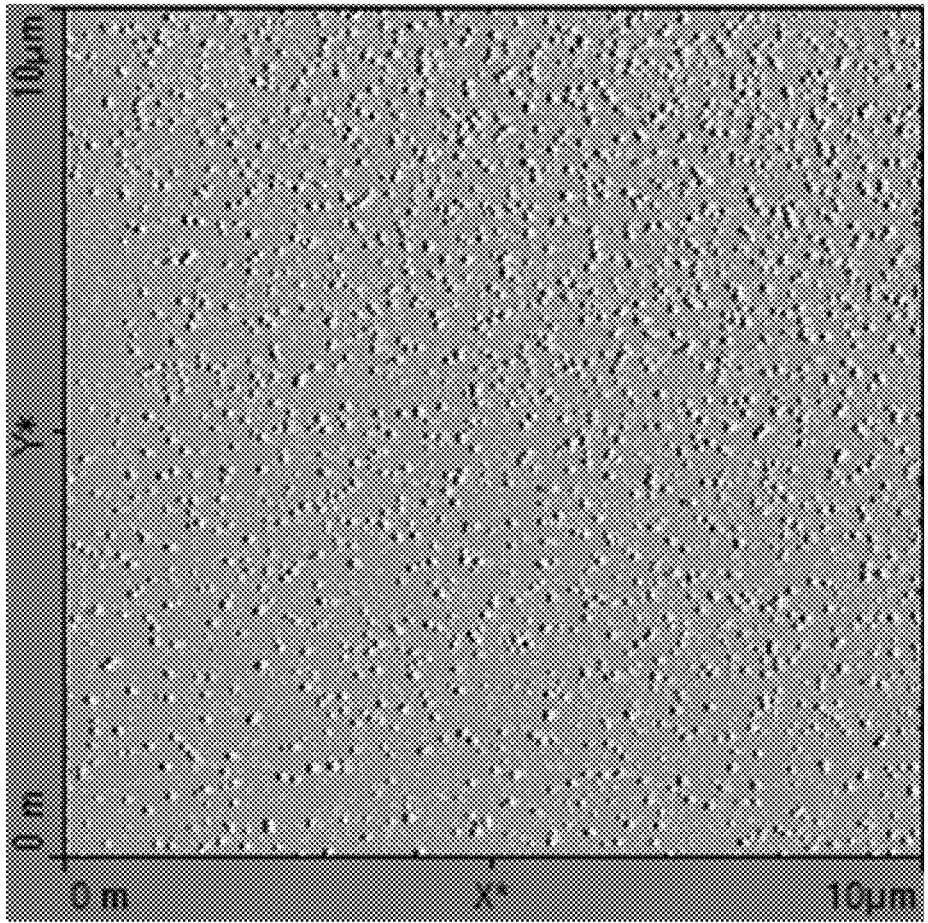

[Fig. 3B]
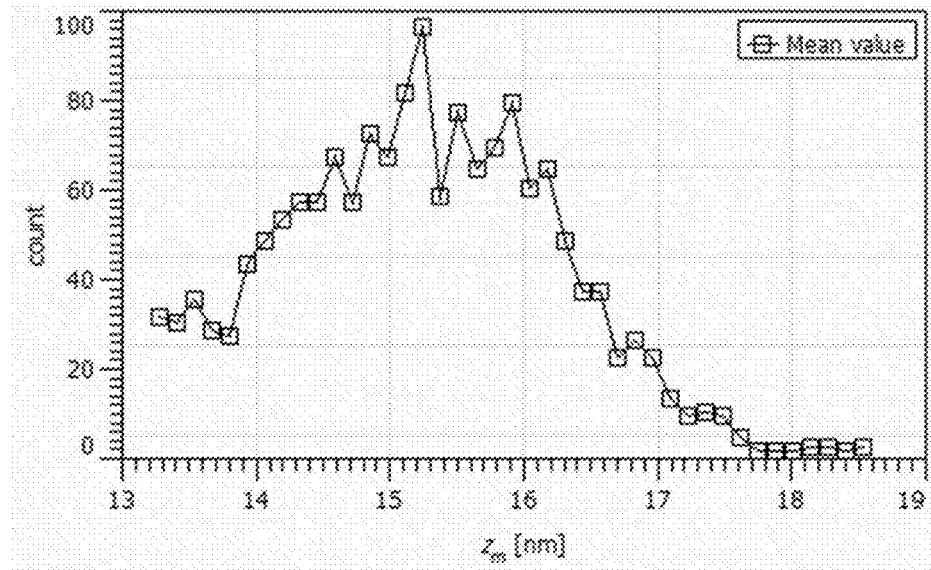
[Fig. 4]
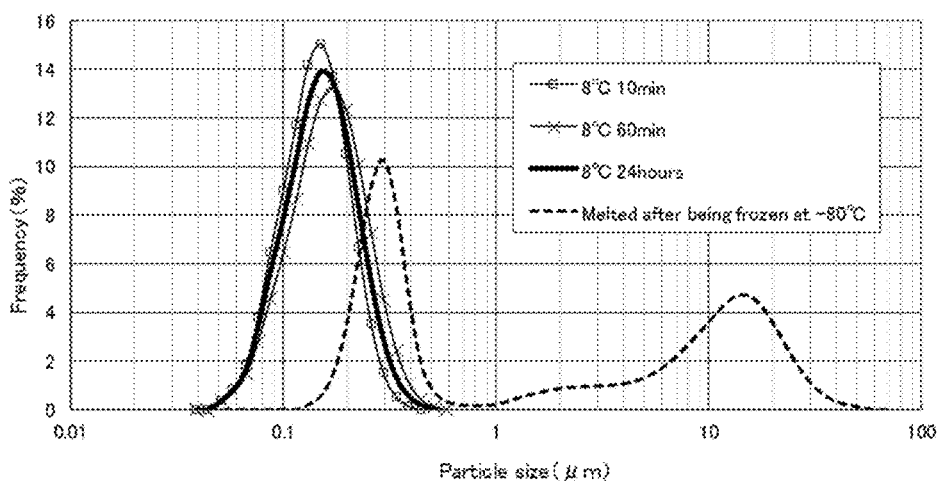

[Fig. 5]
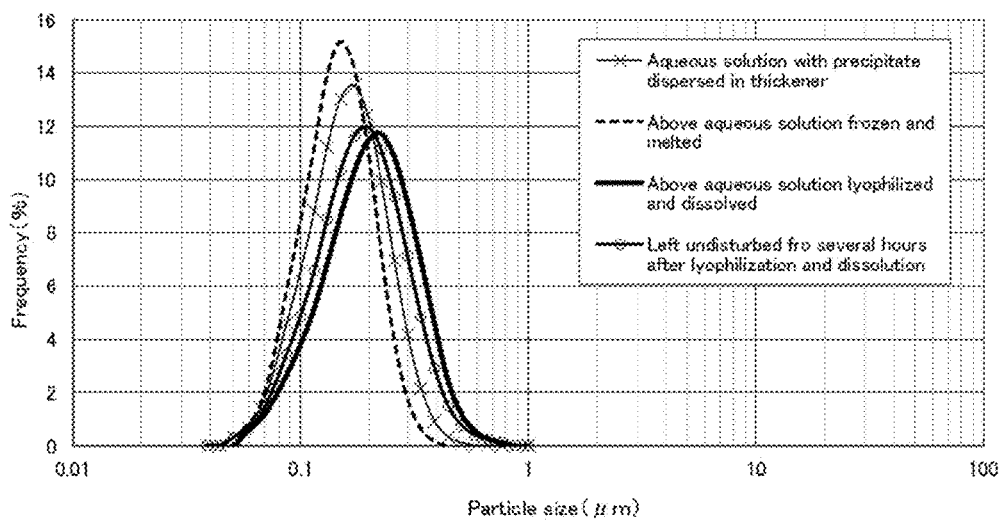
[Fig. 6]
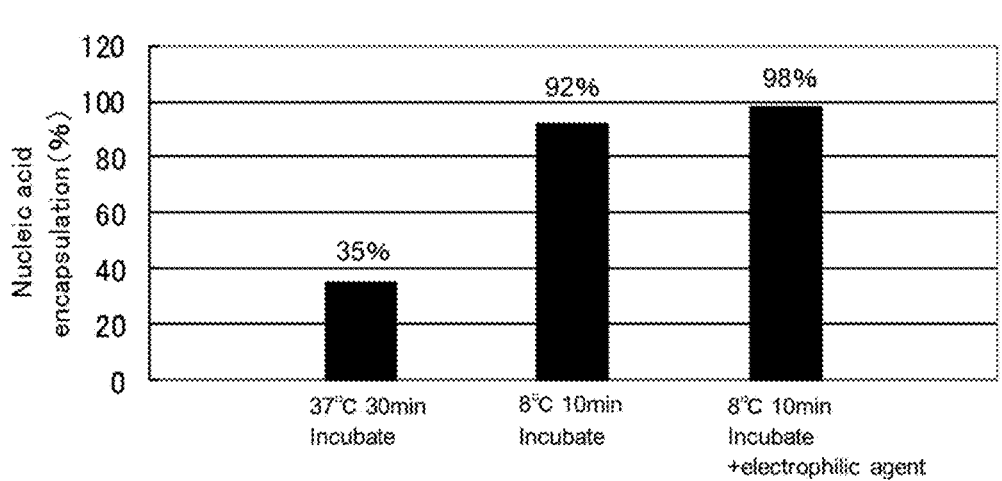

[Fig. 7]
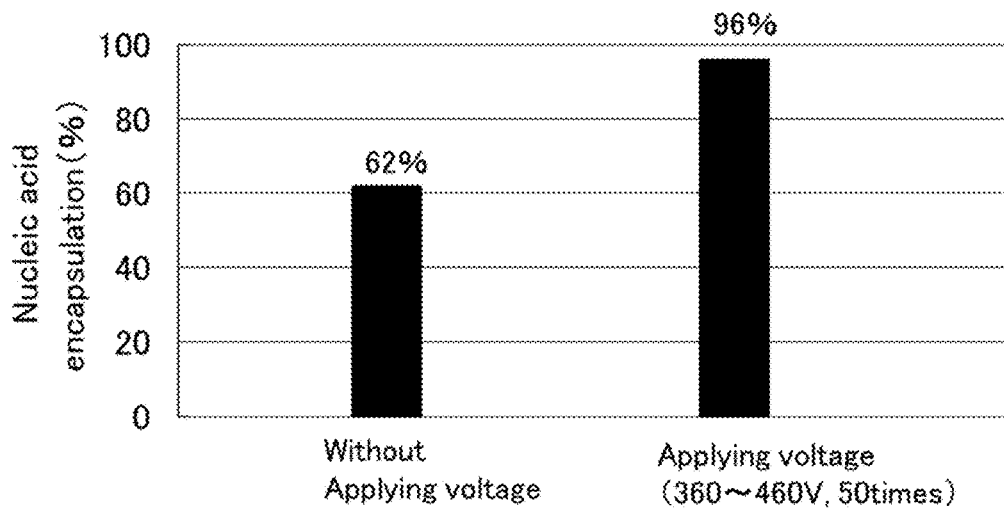
[Fig. 8]
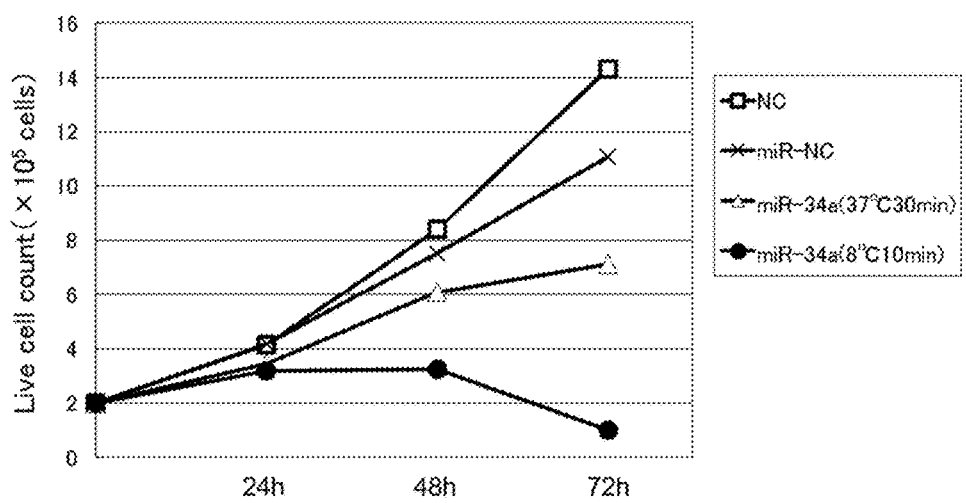

[Fig. 9]
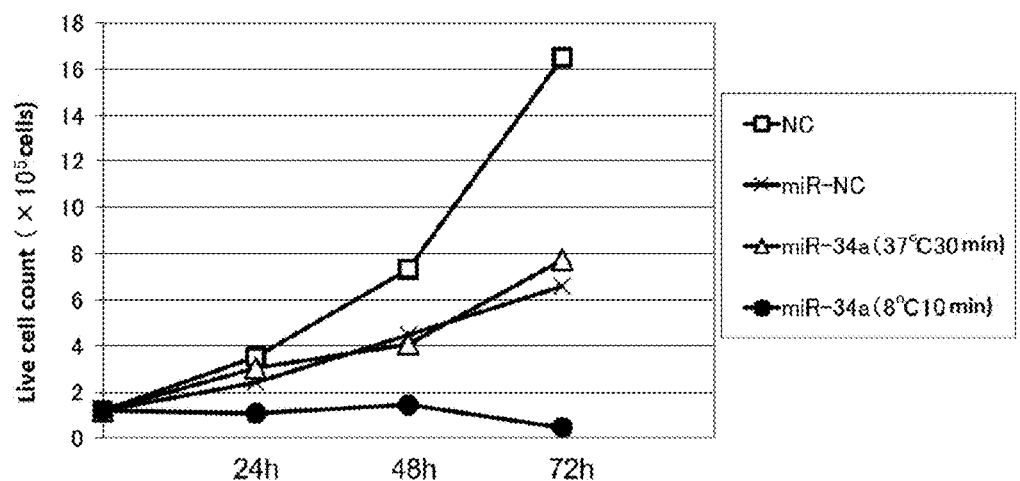
[Fig. 10]
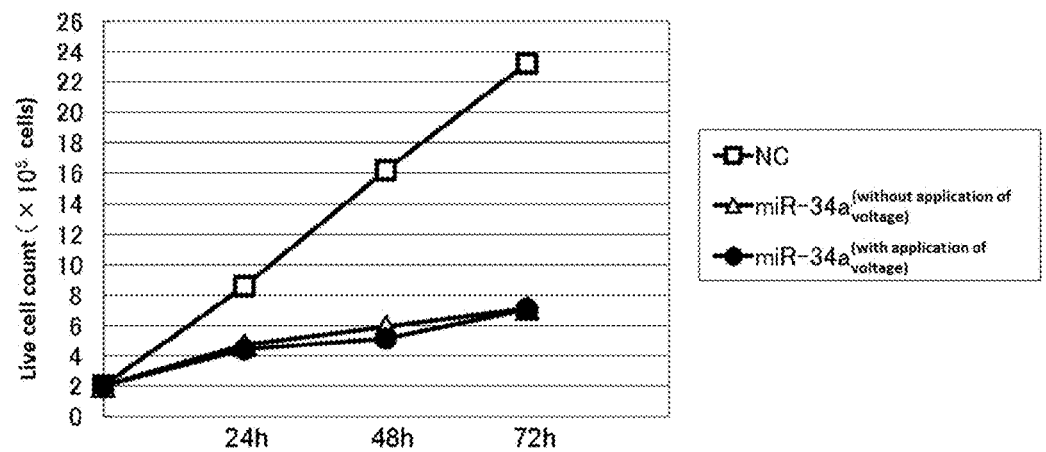

[Fig. 11]
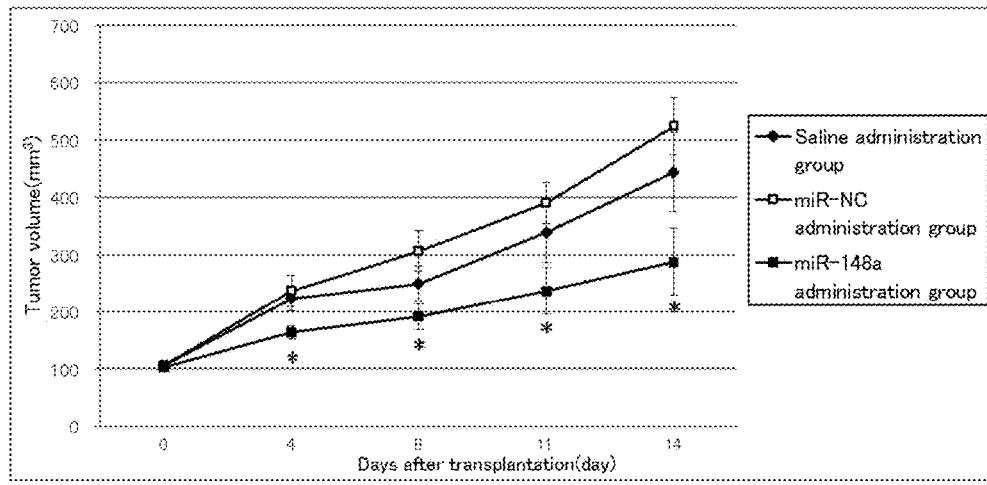
[Fig. 12]
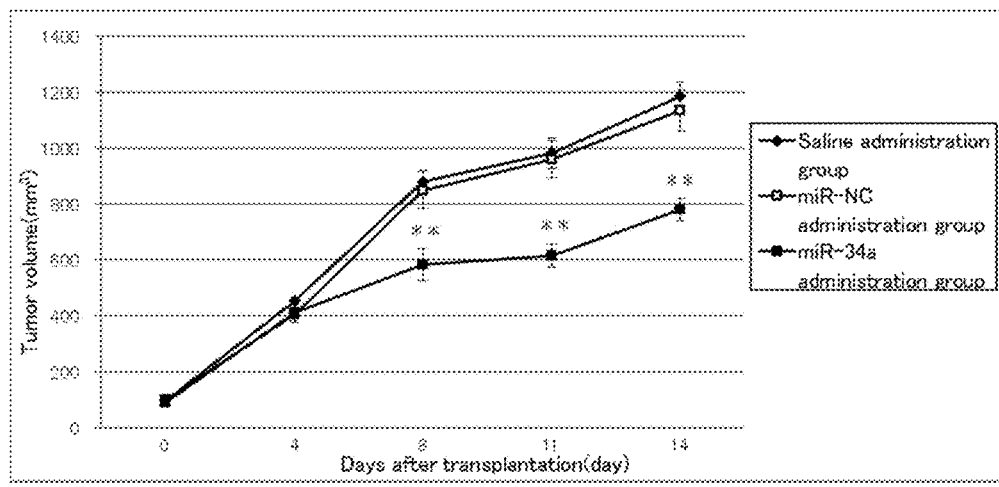

[Fig. 13]
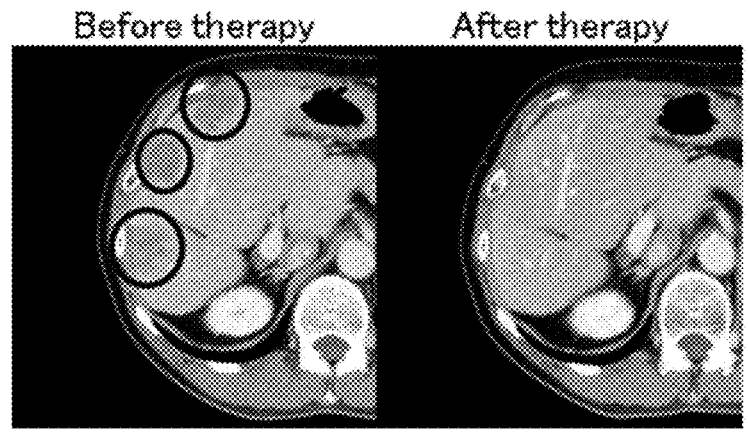
[Fig. 14]
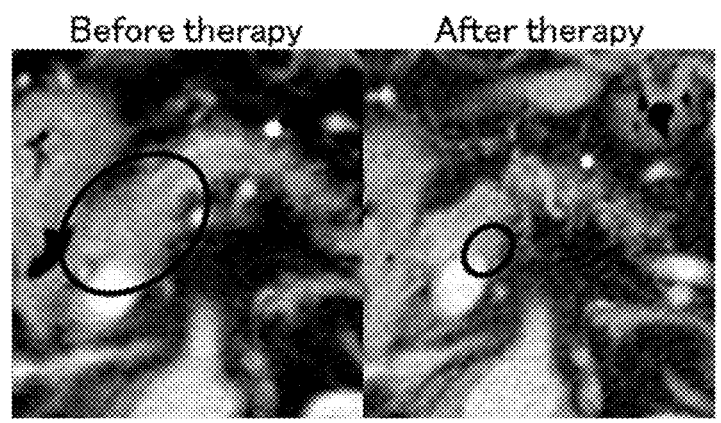
[Fig. 15]
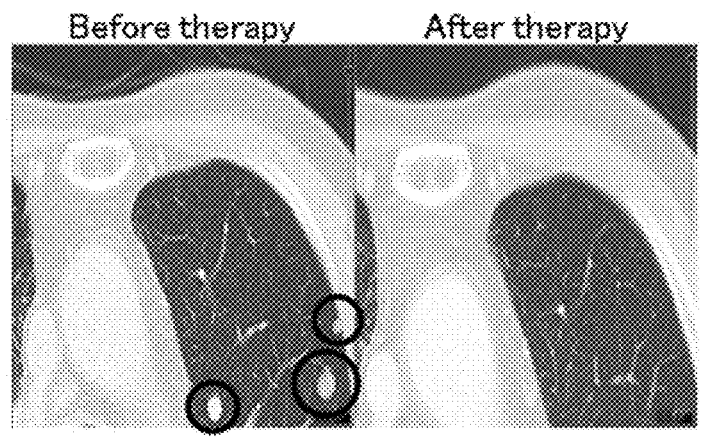

[Fig. 16A]
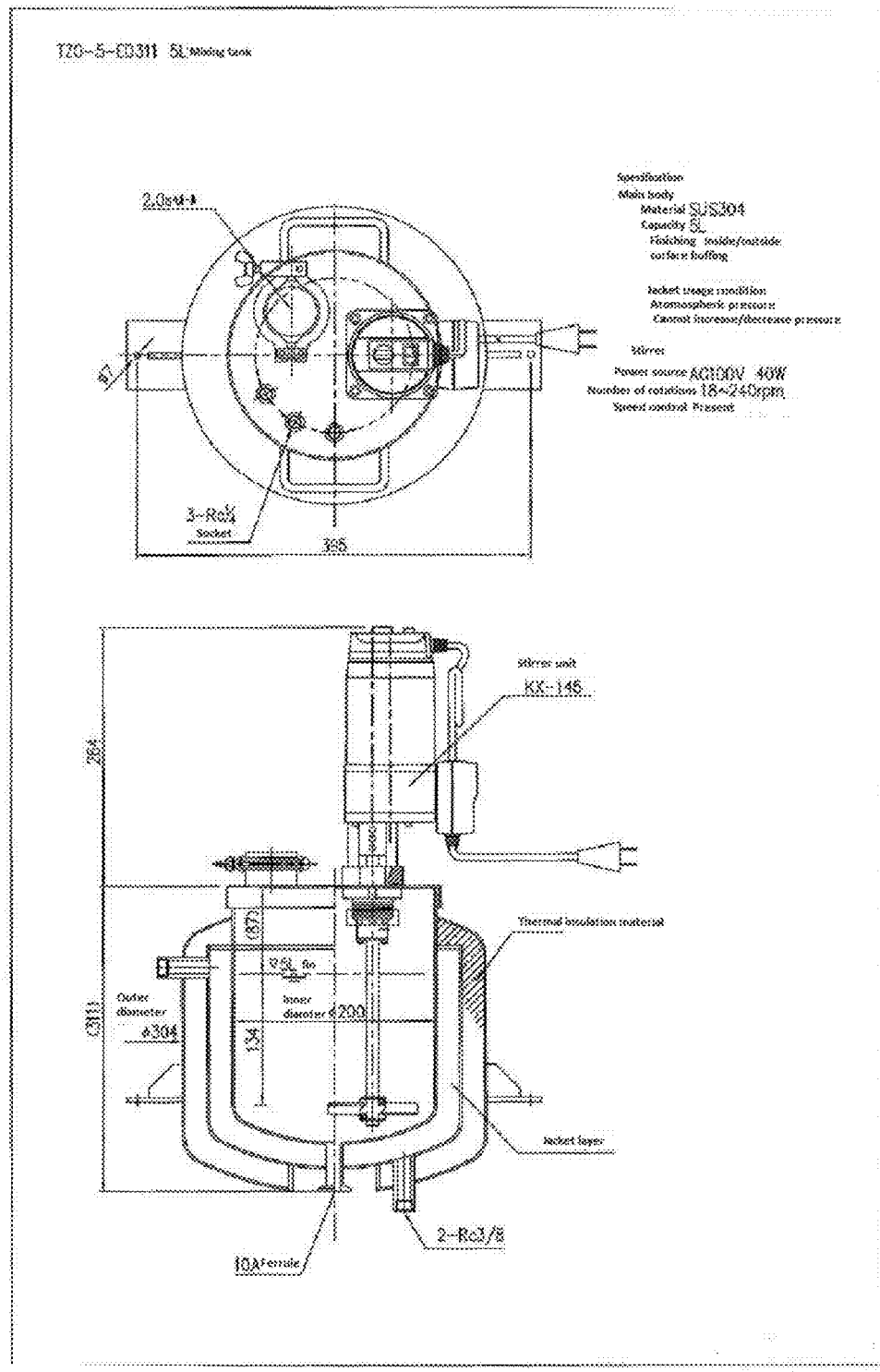

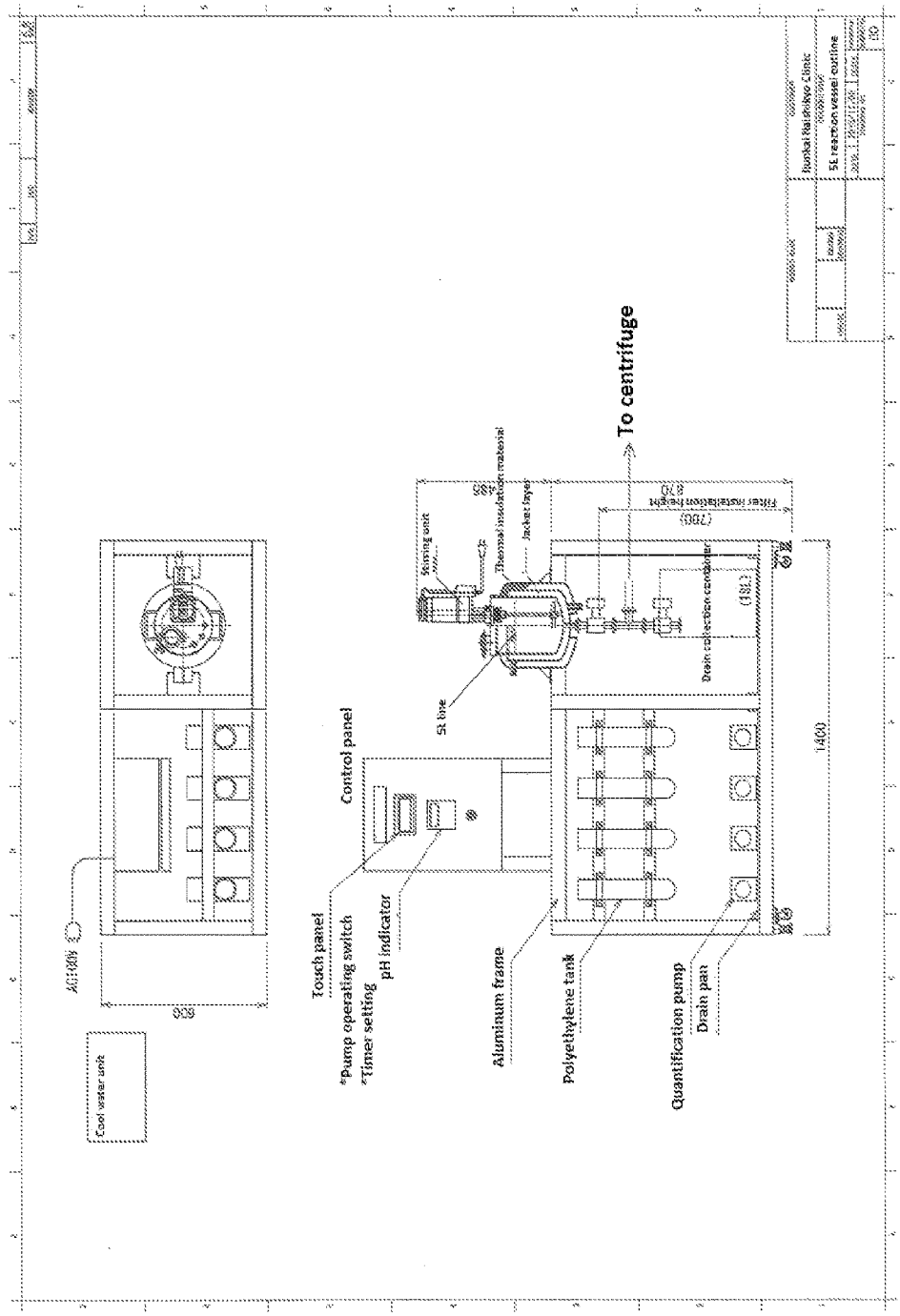
[Fig. 16B]

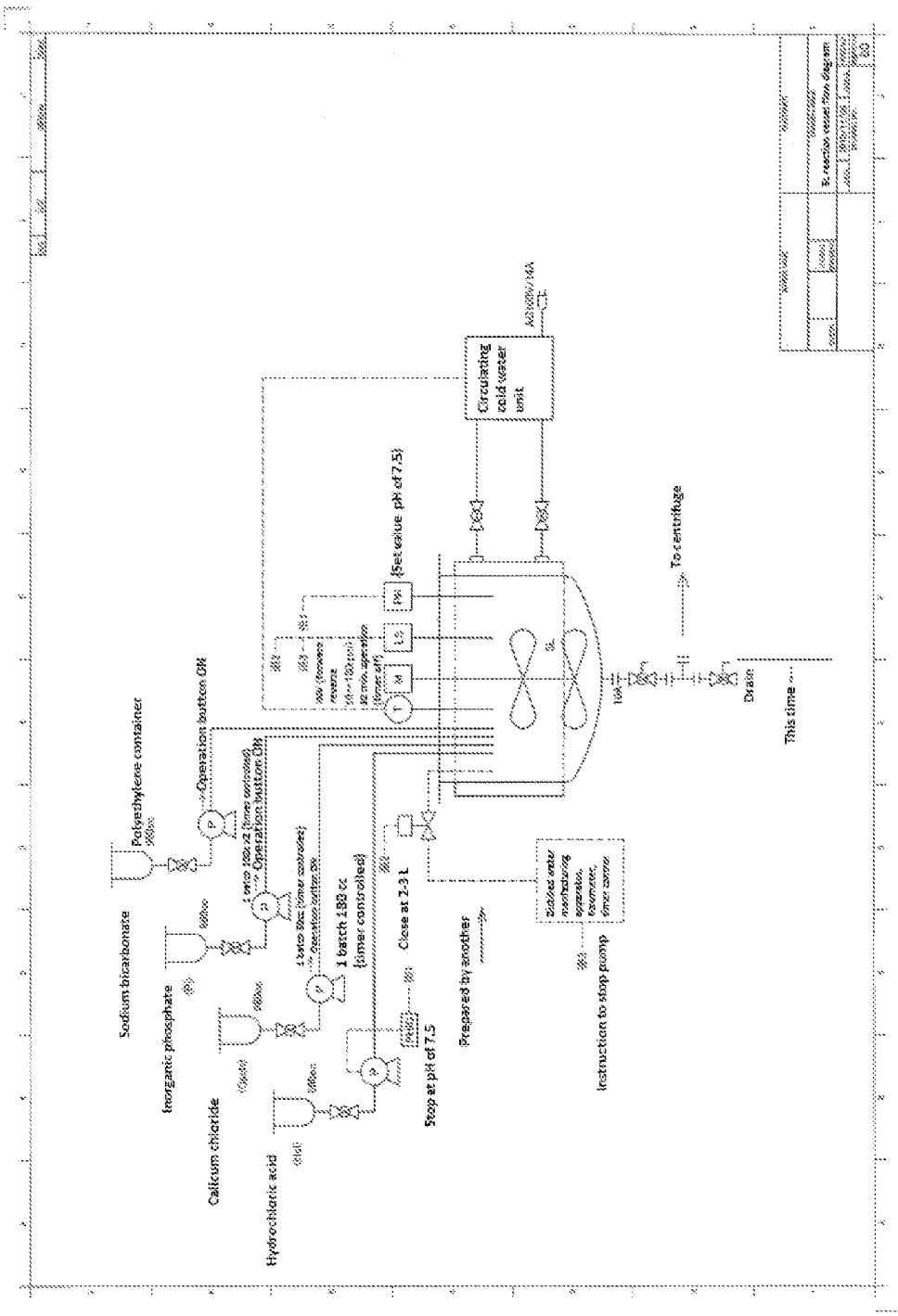
[Fig. 16C]

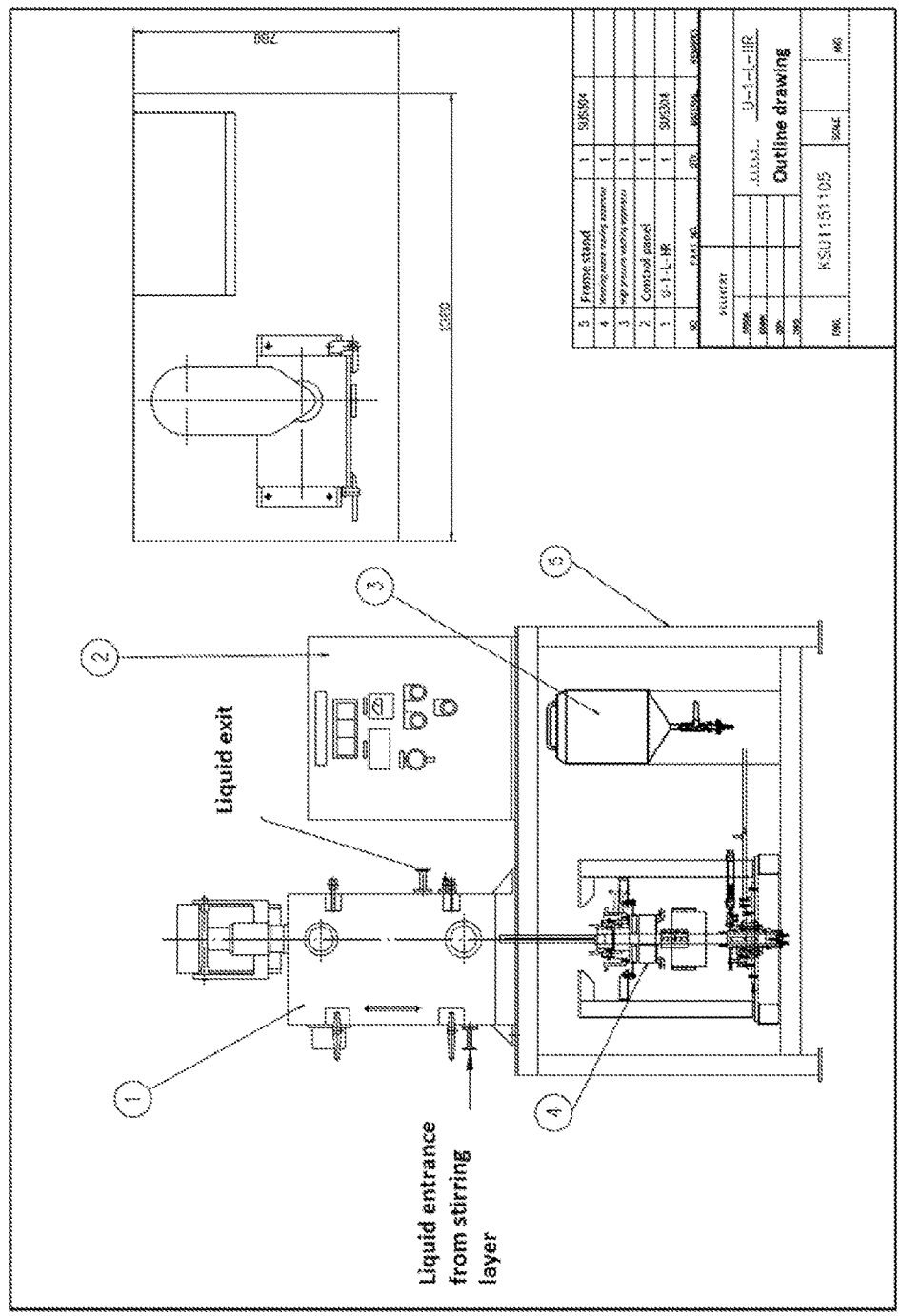
[Fig. 16D]

SEQUENCE LISTING

```
<160> NUMBER OF SEQ ID NOS: 3

<210> SEQ ID NO 1
<211> LENGTH: 22
<212> TYPE: RNA
<213> ORGANISM: Artificial Sequence
<220> FEATURE:
<223> OTHER INFORMATION: miRNA designated as miR-34a based on human
      (Homo sapiens) sequence

<400> SEQUENCE: 1
uggcaguguc uuagcugguu gu                                                  22

<210> SEQ ID NO 2
<211> LENGTH: 22
<212> TYPE: RNA
<213> ORGANISM: Artificial Sequence
<220> FEATURE:
<223> OTHER INFORMATION: miRNA designated as miR-148a based on human
      (Homo sapiens) sequence

<400> SEQUENCE: 2
ucagugcacu acagaacuuu gu                                                  22

<210> SEQ ID NO 3
<211> LENGTH: 22
<212> TYPE: RNA
<213> ORGANISM: Artificial Sequence
<220> FEATURE:
<223> OTHER INFORMATION: miRNA designated as miR-200a based on human
      (Homo sapiens) sequence

<400> SEQUENCE: 3
uaacacuguc ugguaacgau gu                                                  22
```

DRUG INTRODUCING AGENT FOR ADMINISTRATION INTO A LIVING BODY AND MANUFACTURING METHOD

STATEMENT REGARDING SEQUENCE LISTING

The Sequence Listing associated with this application is provided in text format in lieu of a paper copy, and is hereby incorporated by reference into the specification. The name of the text file containing the Sequence Listing is 650099_401_SEQUENCE_LISTING.txt. The text file is 2 KB, was created on Dec. 26, 2016, and is being submitted electronically via EFS-Web.

TECHNICAL FIELD

The present invention relates to a drug introducing agent for the administration of a substance of interest into a living body and a manufacturing method thereof.

BACKGROUND ART

A carbonate apatite has a chemical structure of hydroxylapatite ($Ca_{10}(PO_4)_6(OH)_2$) with some of the hydroxyl groups (OH—) substituted with a carbonate group ($CO_3^{2-}$). Patent Literature 1 proposes the use of a carbonate apatite as a carrier for introducing a substance into a cell. Specifically, Patent Literature 1 discloses an agent for introduction into a cell, wherein when the pH of composite particles comprised of a substance of interest and a calcium phosphate-based material is changed from 8.0 to 6.0, at least 50% of the composite particles that were present at the pH of 8.0 dissolve within a predetermined time from the change to the pH of 6.0. However, carbonate apatites have a problem in that the primary particle size is small, but has an aggregating property such that the secondary particle size is large. Thus, carbonate apatites were insufficient for attaining an EPR effect.

As means for overcoming such a problem, Patent Literature 2 discloses a method of controlling the reaction atmosphere and the amount of carbonic acid in an aqueous solution comprising phosphoric acid and calcium. However, even in view of such conventional art, further improvements were needed for the practical implementation of a carbonate apatite as a carrier for transporting a substance into a cell or a living body.

Large particle size of carbonate apatites leads to safety concerns when administered into a living body. For instance, arteriovenous administration of carbonate apatites with a large particle size leads to issues of intravascular embolism or accumulation in the liver and/or kidney. Further, a particle size that is too small leads to reduced delivery efficiency to cells (or tissue).

Further, the encapsulation rate of drugs in conventional methods is low at around 30%, which was not satisfactory as a agent for introduction into a cell.

CITATION LIST

Patent Literature

[PTL 1] WO 2004/043495
[PTL 2] Japanese Laid-Open Publication No. 2005-75717

SUMMARY OF INVENTION

Technical Problem

For this reason, there is a demand for the provision of a carbonate apatite with a suitable particle size (average particle size and maximum particle size), a small particle size variance ($O^2$), and a high drug encapsulation rate.

Solution to Problem

The inventors solved the above-described problem by providing a method of manufacturing a carbonate apatite using a polymerization reaction at a low temperature and/or in a short period of time.

For example, the present invention provides the following.

(Item 1)
An aqueous solution with a population of carbonate apatites dispersed therein, wherein 90% or more of the population of carbonate apatites have a particle size of 700 nm or less.

(Item 2)
The aqueous solution of item 1, wherein 95% or more of the population of carbonate apatites have a particle size of 700 nm or less.

(Item 3)
The aqueous solution of item 1, wherein 98% or more of the population of carbonate apatites have a particle size of 700 nm or less.

(Item 4)
An aqueous solution with a population of carbonate apatites dispersed therein, wherein the average particle size of the population of carbonate apatites is 30 nm or less.

(Item 5)
The aqueous solution of item 4, wherein the average particle size of the population of carbonate apatites is 20 nm or less.

(Item 6)
The aqueous solution of any one of items 1-5, comprising an emulsifying oily substance.

(Item 7)
The aqueous solution of item 6, comprising 0.5% (w/w) or more of the emulsifying oily substance and having an HLB value of 3-16.

(Item 8)
The aqueous solution of any one of items 1-5, comprising a thickener.

(Item 9)
The aqueous solution of any one of items 1-5, wherein a viscosity is 1.3 mPa·s or more.

(Item 10)
The aqueous solution of any one of items 1-5, wherein the carbonate apatites encapsulate a drug, and an encapsulation rate of the drug is 90% or greater.

(Item 11)
A composition for delivering a drug into a cell, comprising the aqueous solution of any one of items 1-5.

(Item 12)
The composition of item 11, wherein the drug is a medicament.

(Item 13)
The aqueous solution of any one of items 1-5, comprising an electrophilic agent.

(Item 14)
The aqueous solution of any one of items 1-5, comprising a substance having a carbonyl group in a functional group.

(Item 15)
The aqueous solution of any one of items 1-5, comprising a nucleophilic agent.
(Item 16)
The aqueous solution of any one of items 1-5, comprising a substance having an amino group in a function group.
(Item 17)
The aqueous solution of any one of items 13-16, wherein the carbonate apatites encapsulate a drug, and an encapsulation rate of the drug is 98% or greater.
(Item 18)
A method of manufacturing a carbonate apatite encapsulating a drug, the method comprising the step of incubating a mixture comprising a calcium ion, a phosphate ion, a hydrogen carbonate ion, and a drug, wherein an incubation temperature is 10° C. or lower and an incubation time is 10 minutes or less.
(Item 19)
The method of item 18, wherein the incubation time is 1 minute or less.
(Item 20)
The method of item 18 or 19, wherein the mixture comprises an emulsifying oily substance.
(Item 21)
A method of preparing an aqueous solution with carbonate apatites encapsulating a drug dispersed therein, comprising the steps of:
(a) incubating a mixture comprising a calcium ion, a phosphate ion, a hydrogen carbonate ion, and a drug, wherein an incubation temperature is 10° C. or lower and an incubation time is 10 minutes or less;
(b) subjecting the mixture after completion of incubation to high-speed centrifugation; and
(c) dispersing a precipitate obtained by the high-speed centrifugation in an aqueous solution having a viscosity of 1.3 mPa·s or more.
(Item 22)
The method of item 21, wherein the incubation time is 1 minute or less.
(Item 23)
The method of item 21 or 22, wherein the mixture comprises an emulsifying oily substance.
(Item 24)
The method of item 21, wherein a voltage is applied to the mixture at least in a part of step (a).
(Item 25)
A method of manufacturing a carbonate apatite encapsulating a drug, comprising the steps of:
(a) loading water manufactured by an RO water manufacturing apparatus or a distilled water manufacturing apparatus into a stirrer;
(b) loading a phosphate ion and a hydrogen carbonate ion into the stirrer;
(c) adjusting a pH of a mixture loaded in by step (a) and step (b);
(d) loading a calcium ion and a drug into the mixture whose pH was adjusted in step (c) and incubating the resulting mixture at 10° C. or lower for 10 minutes or less;
(e) adding an emulsifying oily substance to the mixture before or after incubating in step (d);
(f) centrifuging a mixture obtained in step (e) in a centrifuge having an inner cylinder applied with polypropylene or an inner cylinder equipped with a polypropylene cylinder to obtain a precipitate; and
(g) spraying a substance selected from the group consisting of air, distilled water, saline, and a thickener with a nozzle that is automatically inserted from a top or bottom portion of the cylinder and collecting the precipitate obtained in step (f).
(Item 26)
The method of item 25, further comprising the step of:
(h) bottling and lyophilizing the precipitate collected in step (g).
(Item 27)
A pharmaceutical composition for treating or preventing cancer, comprising the aqueous solution of any one of items 1-5, wherein the carbonate apatites encapsulate a drug.

For example, the present invention also provides the following:
(Item A1)
A method of administrating a drug, comprising the step of administering a composition comprising carbonate apatites encapsulating the drug, wherein 90% or more of a population of the carbonate apatites have a particle size of 700 nm or less.
(Item A2)
The method of item A1, wherein 95% or more of the population of carbonate apatites have a particle size of 700 nm or less.
(Item A3)
The method of item A1, wherein 98% or more of the population of carbonate apatites have a particle size of 700 nm or less.
(Item A4)
The method of item A1, wherein the average particle size of the population of carbonate apatites is 30 nm or less.
(Item A5)
The method of item A1, wherein the average particle size of the population of carbonate apatites is 20 nm or less.
(Item A6)
The method of item A1, wherein the composition comprises an emulsifying oily substance.
(Item A7)
The method of item A6, wherein the composition comprises 0.5% (w/w) or more of the emulsifying oily substance and the composition has an HLB value of 3-16.
(Item A8)
The method of item A1, wherein the composition comprises a thickener.
(Item A9)
The method of item A1, wherein a viscosity of the composition is 1.3 mPa·s or more.
(Item A10)
The method of item A1, wherein an encapsulation rate of the drug in the composition is 90% or greater.
(Item A11)
The method of item A1, wherein the composition comprises an electrophilic agent.
(Item A12)
The method of item A1, wherein the composition comprises a nucleophilic agent.
(Item A13)
The method of item A1, wherein the drug is an miRNA.
(Item A14)
A method of treating or preventing cancer, comprising the step of administering a composition comprising carbonate apatites encapsulating a drug, wherein 90% or more of a population of the carbonate apatites have a particle size of 700 nm or less.
(Item A15)
The method of item A14, wherein the drug is an miRNA.

(Item A16)

The method of item A14, wherein the drug is an anticancer agent.

(Item A17)

A method of manufacturing a carbonate apatite encapsulating a drug, the method comprising the step of incubating a mixture comprising a calcium ion, a phosphate ion, a hydrogen carbonate ion, and a drug, wherein an incubation temperature is 10° C. or lower and an incubation time is 10 minutes or less.

(Item A18)

The method of item A17, wherein the incubation time is 1 minute or less.

(Item A19)

The method of item A17, wherein the mixture comprises an emulsifying oily substance.

(Item A20)

A method of preparing an aqueous solution with carbonate apatites encapsulating a drug dispersed therein, comprising the steps of:
(a) incubating a mixture comprising a calcium ion, a phosphate ion, a hydrogen carbonate ion, and a drug, wherein an incubation temperature is 10° C. or lower and an incubation time is 10 minutes or less;
(b) subjecting the mixture after completion of incubation to high-speed centrifugation; and
(c) dispersing a precipitate obtained by the high-speed centrifugation in an aqueous solution having a viscosity of 1.3 mPa·s or more.

(Item A21)

The method of item A20, wherein the incubation time is 1 minute or less.

(Item A22)

The method of item A20, wherein the mixture comprises an emulsifying oily substance.

(Item A23)

The method of item A20, wherein a voltage is applied to the mixture at least in a part of step (a).

(Item A24)

A method of manufacturing a carbonate apatite encapsulating a drug, comprising the steps of:
(a) loading water manufactured by an RO water manufacturing apparatus or a distilled water manufacturing apparatus into a stirrer;
(b) loading a phosphate ion and a hydrogen carbonate ion into the stirrer;
(c) adjusting a pH of a mixture loaded in by step (a) and step (b);
(d) loading a calcium ion and a drug into the mixture whose pH was adjusted in step (c) and incubating the resulting mixture at 10° C. or lower for 10 minutes or less;
(e) adding an emulsifying oily substance to the mixture before or after incubating in step (d);
(f) centrifuging a mixture obtained in step (e) in a centrifuge having an inner cylinder applied with polypropylene or an inner cylinder equipped with a polypropylene cylinder to obtain a precipitate; and
(g) spraying a substance selected from the group consisting of air, distilled water, saline, and a thickener with a nozzle that is automatically inserted from a top or bottom portion of the cylinder and collecting the precipitate obtained in step (f).

(Item A25)

The method of item A24, further comprising the step of:
(h) bottling and lyophilizing the precipitate collected in step (g).

Advantageous Effects of Invention

The present invention provides carbonate apatites with a suitable particle size (average particle size and maximum particle size), small particle size variance ($\sigma^2$), and high drug encapsulation rate. Use of the carbonate apatites of the present invention allows for highly efficient and safe delivery of drugs into cells.

BRIEF DESCRIPTION OF DRAWINGS

FIG. 1 is a graph showing a comparison of particle sizes of carbonate apatites manufactured by using incubation under a low temperature (8° C.) or a high temperature (37° C.).

FIG. 2 is a graph showing the frequencies of particle sizes over time of carbonate apatites manufactured by using various incubation times at a low temperature (8° C.).

FIG. 3A is an image from an atomic force microscope (AFM) of carbonate apatite particles produced by incubation at 8° C. for 1 minute.

FIG. 3B is a graph showing the frequency of particles having each Zm.

FIG. 4 is a graph showing the frequencies of particle sizes over time of carbonate apatites manufactured by using an emulsifying oily material.

FIG. 5 is a graph showing the frequencies of particle sizes of carbonate apatites manufactured by using a thickener.

FIG. 6 is a graph showing nucleic acid encapsulation rates due to a reaction in a low temperature, short incubation and addition of an electrophilic agent.

FIG. 7 is a graph showing nucleic acid encapsulation rates due to application of voltages in a low temperature, short incubation.

FIG. 8 is a graph showing results of an antitumor cell experiment using a human lung cancer cell line by the nucleic acid encapsulating carbonate apatites of the present invention.

FIG. 9 is a graph showing results of an antitumor cell experiment using a human colonic adenocarcinoma cell line by the nucleic acid encapsulating carbonate apatites of the present invention.

FIG. 10 is a graph showing results of an antitumor cell experiment using a human colonic adenocarcinoma cell line when using a nucleic acid encapsulation carbonate apatite manufactured by applying a voltage.

FIG. 11 is a graph showing results of an antitumor effect experiment using a cancer-bearing nude mouse made by using a human gastric cancer cell line.

FIG. 12 is a graph showing results of an antitumor effect experiment using a cancer-bearing nude mouse made by using a human colonic adenocarcinoma cell line.

FIG. 13 is a picture showing results of a clinical trial targeting a 63 years old male with colon cancer/multiple liver metastasis.

FIG. 14 is a picture showing results of a clinical trial targeting a 76 years old male with pancreatic cancer.

FIG. 15 is a picture showing results of a clinical trial targeting a 55 years old male with esophageal cancer/multiple lung metastasis.

FIG. 16A is a manufacturing apparatus (stirrer) for manufacturing the nucleic acid encapsulating carbonate apatite of the invention.

FIG. 16B is a manufacturing apparatus (reactor) for manufacturing the nucleic acid encapsulating carbonate apatite of the invention.

FIG. 16C is a manufacturing apparatus (reactor) for manufacturing the nucleic acid encapsulating carbonate apatite of the invention.

FIG. 16D is a manufacturing apparatus (centrifuge) for manufacturing the nucleic acid encapsulating carbonate apatite of the invention.

DESCRIPTION OF EMBODIMENTS

The present invention is described hereinafter. The terms used herein should be understood to be used in the meaning that is commonly used in the art, unless specifically noted otherwise. Thus, unless defined otherwise, all terminologies and scientific technical terms that are used herein have the same meaning as the terms commonly understood by those skilled in the art pertaining to the present invention. In case of a contradiction, the present specification (including the definitions) takes precedence. As used herein, "%" refers to % by weight (w/w %) unless specifically noted otherwise.

Definition of Terms

The composition itself of "carbonate apatite" used in the present invention is known. A carbonate apatite has a chemical structure of hydroxylapatite ($Ca_{10}(PO_4)_6(OH)_2$) with some of the hydroxyl groups (OH—) substituted with a carbonate group ($CO_3^{2-}$). Carbonate apatites are represented by the general formula $Ca_{10-m}X_m(PO_4)_6(CO_3)_{1-n}Y_n$. In the general formula, X may be any element that can partially substitute Ca in a carbonate apatite. Examples thereof include Sr, Mn, rare earth elements and the like. Generally, m is a positive number that is greater than or equal to 0 and less than or equal to 1, preferably greater than or equal to 0 and less than or equal to 0.1, more preferably greater than or equal to 0 and less than or equal to 0.01, and still more preferably greater than or equal to 0 and less than or equal to 0.001. Y is a unit that can partially substitute $CO_3$ in a carbonate apatite. Examples thereof include OH, F, CI and the like. Generally, n is a positive number that is greater than or equal to 0 and less than or equal to 0.1, preferably greater than or equal to 0 and less than or equal to 0.01, more preferably greater than or equal to 0 and less than or equal to 0.001, and still more preferably greater than or equal to 0 and less than or equal to 0.0001. The carbonate apatite of the present invention is typically characterized by having a property where, when the pH of composite particles is changed, for example, from 8.0 to of 6.0, at least 50% of the composite particles that were present at the pH of 8.0 dissolve within a predetermined time from the change to the pH of 6.0.

As used herein, "carbonate apatite" can encapsulate a "drug" such that a pharmaceutical composition or medicinal composition can be produced. Those skilled in the art can utilize the pharmaceutical composition or medicinal composition of the present invention, upon preparation, in therapy or prevention of various diseases including cancer. In the present invention, it is possible to select a drug that is suitable for the disease and/or condition of interest for therapy and/or prevention.

As used herein, the term "particle size" refers to a value that is measured based on volume by using a laser diffraction analyzer. This measurement measures the particle size of independent particles recognizable as separate particles. Thus, when multiple particles are aggregated, an assembly thereof is judged to be a single particle.

As used herein, the term "average particle size" refers to the average value of particle sizes of all particles measured by using an atomic force microscope (AFM) at a measurement site.

As used herein, the term "emulsifying oily substance" refers to any oily (hydrophobic) component or amphiphilic component suitable for administration into a cell which has the ability to emulsify. Examples of emulsifying oily substances used in the present invention include, but are not limited to, Intralipos® with an effective ingredient of purified soybean oil, ethyl icosapentate, and phospholipid PEG (substance comprising PEG bound to phospholipid). Further, an appropriate combination thereof may also be used.

As used herein, the term "thickener" refers to any substance suitable for administration into a cell which increases the viscosity of an aqueous solution. Examples of the thickener used in the present invention include, but are not limited to, saccharides such as glucose, sucrose, lactose, glycerin, fructose, xylitol, and trehalose and PEG. Further, an appropriate combination thereof may also be used.

As used herein, the term "drug" refers to any substance intended to be delivered to a cell and/or tissue. A drug may also be a medicament (e.g., substance exerting a pharmacological effect). Examples of the drugs used in the present invention include, but are not limited to, nucleic acids (nucleic acid medicines) such as DNA, RNA, antisense RNA, siRNA, and miRNA, enzymes, peptides or proteins, polypeptides such as various peptidic hormones, antimetabolites such as fluorouracil, alkylating agents such as cyclophosphamide, platinum formulations such as cisplatin, molecule targeting drugs such as bevacizumab, various anticancer agents such as topoisomerase inhibitors (irinotecan), various antibiotics, hormonal agents, vitamins, antiallergic agents, therapeutic agents for a central nervous system disease, therapeutic agents for a circulatory organ disease, therapeutic agents for a respiratory organ system disease, therapeutic agents for a digestive organ system disease, therapeutic agents for a urogenital organ disorder, and the like. Further, an appropriate combination of multiple drugs may also be used.

As used herein, the term "encapsulation rate of a drug" refers to the ratio of the drug carried by a carbonate apatite to total amount of drug loaded. For instance, the encapsulation rate is calculated by (amount of drug carried by carbonate apatite)/(total amount of loaded drug). Preferably, the encapsulation rate of a drug in the present invention is 70% or greater, 80% or greater, 90% or greater, 95% or greater, or 98% or greater.

As used herein, the term "electrophilic agent" refers to a drug on the electron receiving end in a reaction that generates a chemical reaction while giving and receiving electrons between different chemical species. Examples of electrophilic agents used in the present invention include, but are not limited to, substances having a carbonyl group in a functional group, such as acetaminophen, acetosalicylic acid, ascorbic acid, and diazepam. Further, an appropriate combination thereof may also be used. Although not wishing to be bound by any theory, a negatively charged drug (e.g., nucleic acid) is drawn closer by an electrophilic agent and encapsulated in a particle. Among such electrophilic agents, it is understood that the effect is particularly significant for substances with a carbonyl group in a functional group.

As used herein, the term "nucleophilic agent" refers to a drug on the electron providing end in a reaction that generates a chemical reaction while giving and receiving electrons between different chemical species. Examples of nucleophilic agents used in the present invention include, but are not limited to, substances having an amino group in a functional group, such as glycine, adrenaline, noradrenaline, and dopamine. Further, an appropriate combination thereof may also be used. Although not wishing to be bound by any theory, a positively charged drug (e.g., anticancer agent) is drawn closer by a nucleophilic agent and encapsulated in a particle. Among such nucleophilic agents, it is understood that the effect is particularly significant for substances with an amino group in a functional group.

The source of "calcium ion" used in the manufacture of a carbonate apatite in the present invention is not particularly limited. Examples thereof include, but are not limited to, calcium chloride.

The source of "phosphate ion" used in the manufacture of a carbonate apatite in the present invention is not particularly limited. Examples thereof include, but are not limited to, sodium dihydrogen phosphate dihydrate.

The source of "hydrogen carbonate ion" used in the manufacture of a carbonate apatite in the present invention is not particularly limited. Examples thereof include, but are not limited to, sodium bicarbonate.

Examples of pH for incubating a mixture comprising a calcium ion, phosphate ion, and hydrogen carbonate ion in the manufacture of a carbonate apatite in the present invention include, but are not limited to, a pH of 6.0-9.0, pH of 7.0-8.0, and pH of about 7.5.

Examples of preferred incubation temperatures used in the manufacture of a carbonate apatite in the present invention include, but are not limited to, 10° C. or lower, 9° C. or lower, 8° C. or lower, 7° C. or lower, 6° C. or lower, 5° C. or lower, 4° C. or lower, 3° C. or lower, and 2° C. or lower. However, it is preferable to avoid freezing mixtures, so that temperatures such as 1° C. or higher, 2° C. or higher, 3° C. or higher, 4° C. or higher, 5° C. or higher, 6° C. or higher, or 7° C. or higher is used.

The average particle size would be small when a low incubation temperature is used in the manufacture of a carbonate apatite of the present invention. Thus, the particle size of the produced carbonate apatite can be controlled by adjusting the incubation temperature. Although not wishing to be bound by any theory, it is understood that this is due to incubation at a lower temperature suppressing Brownian motion of particles, resulting in suppression of particle aggregation.

Examples of preferred incubation times used in the manufacture of a carbonate apatite of the present invention include, but are not limited to, 10 minutes or less, 9 minutes or less, 8 minutes or less, 7 minutes or less, 6 minutes or less, 5 minutes or less, 4 minutes or less, 3 minutes or less, 2 minutes or less, 90 seconds or less, 75 seconds or less, 60 seconds or less, 45 seconds or less, and 30 seconds or less. Further, incubation time is preferably 10 seconds or more, 15 seconds or more, 20 seconds or more, 25 seconds or more, 30 seconds or more, 35 seconds or more, 40 seconds or more, 45 seconds or more, 50 seconds or more, and 55 seconds or more. Although not wishing to be bound by any theory, when the incubation temperature is for example 8° C., it is understood that a carbonate apatite producing reaction is completed in about 1 minute or less, while an aggregation reaction is promoted thereafter.

A reaction (incubation) used in the manufacture of a carbonate apatite of the present invention can be initiated, for example, by adding a calcium ion to a mixture comprising a phosphate ion and a hydrogen carbonate ion. Further, incubation can be ended by adding a thickener and/or emulsifying oily substance to an incubation mixture. However, a production reaction is mostly completed in a short period of time of 1 minute or less. Thus, an emulsifying oily substance or thickener may be added from the start.

The concentration of an emulsifying oily substance in the aqueous solution comprising a carbonate apatite of the present invention is typically 0.1% (w/w) or greater, 0.2% (w/w) or greater, 0.3% (w/w) or greater, 0.4% (w/w) or greater, 0.5% (w/w) or greater, 0.6% (w/w) or greater, 0.7% (w/w) or greater, 0.8% (w/w) or greater, 0.9% (w/w) or greater, 1.0% (w/w) or greater, or 2.0% (w/w) or less, 1.8% (w/w) or less, 1.6% (w/w) or less, 1.4% (w/w) or less, 1.2% (w/w) or less, 1.0% (w/w) or less, 0.8% (w/w) or less, or 0.6% (w/w) or less. The HLB value of an emulsifying oily substance is typically 3-16 and preferably 6-10. Although not wishing to be bound by any theory, it is understood that, particle formation, being a chemical reaction, is completed almost instantaneously, such that addition of an emulsifying oily substance before or after the reaction halts the reaction during ultrafine particle formation to suppress aggregation.

In a population of carbonate apatites contained in the aqueous solution of the present invention, 90% or more of the population has a particle size of 700 nm or less, 95% or more of the population has a particle size of 700 nm or less, 98% or more of the population has a particle size of 700 nm or less, 99% or more of the population has a particle size of 700 nm or less, 90% or more of the population has a particle size of 600 nm or less, 95% or more of the population has a particle size of 600 nm or less, 98% or more of the population has a particle size of 600 nm or less, 99% or more of the population has a particle size of 600 nm or less, 90% or more of the population has a particle size of 500 nm or less, 95% or more of the population has a particle size of 500 nm or less, 98% or more of the population has a particle size of 500 nm or less, 99% or more of the population has a particle size of 500 nm or less, 90% or more of the population has a particle size of 400 nm or less, 95% or more of the population has a particle size of 400 nm or less, 98% or more of the population has a particle size of 400 nm or less, or 99% or more of the population has a particle size of 400 nm or less.

To accomplish the particle size shown above which is the characteristic of a population of carbonate apatites of the present invention, it is not necessary to treat the carbonate apatites with an ultrasound wave. Since ultrasound wave treatment destroys a carbonate apatite particle, the particle size of the carbonate apatite can be made smaller. However, particles are not uniformly destroyed. As a result, particles sizes of each carbonate apatite particle contained in a population of carbonate apatites significantly vary. Variation in particle sizes would be a significant disadvantage in use as a medicinal composition/pharmaceutical composition. Particles of carbonate apatites treated with ultrasound waves readily aggregate. For this reason, it is necessary to administer a carbonate apatite treated with ultrasound waves quickly when used as a medicinal composition/pharmaceutical composition. For instance, further size fractionation by filtering or the like would be difficult. In contrast, the population of carbonate apatites of the present invention is not treated with ultrasound waves, such that the population would not aggregate even after being left undisturbed for several minutes or longer or several tens of minutes or longer. For instance, the aforementioned characteristic of the particle size of the population of carbonate apatites of the present invention is maintained even after leaving the carbonate apatite population of the present invention undisturbed, for example, for 5 minutes, 10 minutes, 15 minutes, 20 minutes, 30 minutes, 45 minutes, or 60 minutes at room temperature (e.g., 25° C.).

Further, since the carbonate apatite of the present invention does not require ultrasound wave treatment, it would not aggregate even if left undisturbed for several minutes or more or several tens of minutes or more at room temperature (maintain a dispersed state in a solution). Thus, it is not necessary to add albumin for preventing aggregation (to maintain a dispersed state in a solution). Thus, a solution in which carbonate apatites of the present invention are dispersed therein is preferably a solution that is free or substantially free of albumin. The medicinal composition/pharmaceutical composition made by the present invention, due to being free of albumin, can avoid the risk of a disease caused by albumin.

The average particle size of a population of carbonate apatites contained in the aqueous solution of the present invention is 50 nm or less, 40 nm or less, 30 nm or less, 20 nm or less, 15 nm or less, 10 nm or less, 7 nm or less, or 5 nm or less.

The variance "$\sigma^2$" of the particle sizes of a population of carbonate apatites contained in the aqueous solution of the present invention is preferably 0.1 or less, more preferably 0.05 or less, and still more preferably 0.01 or less, but not limited thereto.

The aqueous solution of carbonate apatites of the present invention can be prepared, for example, by dispersing a carbonate apatite precipitation obtained by high-speed centrifugation in an aqueous solution. Examples of viscosity of an aqueous solution where the carbonate apatite is dispersed include, but are not limited to, 0.5 mPa·s or greater, 0.6 mPa·s or greater, 0.7 mPa·s or greater, 0.8 mPa·s or greater, 0.9 mPa·s or greater, 1.0 mPa·s or greater, 1.1 mPa·s or greater, 1.2 mPa·s or greater, 1.3 mPa·s or greater, 1.4 mPa·s or greater, 1.5 mPa·s or greater, 1.6 mPa·s or greater, 1.7 mPa·s or greater, 1.8 mPa·s or greater, and 5.0 mPa·s or less, 4.5 mPa·s or less, 4.0 mPa·s or less, 3.5 mPa·s or less, 3.0 mPa·s or less, 2.9 mPa·s or less, 2.8 mPa·s or less, 2.7 mPa·s or less, 2.6 mPa·s or less, 2.5 mPa·s or less, 2.4 mPa·s or less, 2.3 mPa·s or less, 2.2 mPa·s or less, 2.1 mPa·s or less, and 2.0 mPa·s.

Examples of high-speed centrifugation used in the present invention include, are not limited to, 8,000 G or greater, 9,000 G or greater, 10,000 G or greater, 11,000 G or greater, 12,000 G or greater, 13,000 G or greater, and 14,000 G or greater, such as 8,000 G, 9,000 G, 10,000 G, 11,000 G, 12,000 G, 13,000 G, and 14,000 G.

While the method of manufacturing a carbonate apatite encapsulating a drug is not limited to a particular method, a carbonate apatite encapsulating a drug can be manufactured by a method comprising the steps of:

(a) loading water manufactured by an RO water manufacturing apparatus or a distilled water manufacturing apparatus into a stirrer;
(b) loading a phosphate ion and a hydrogen carbonate ion into the stirrer;
(c) adjusting a pH of a mixture loaded in by step (a) and step (b);
(d) loading a calcium ion and a drug into the mixture whose pH was adjusted in step (c) and incubating the resulting mixture at a low temperature (e.g., about 10° C., about 9° C., about 8° C., about 7° C., about 6° C., about 5° C., about 4° C., about 3° C., or about 2° C.) for a short period of time (e.g., 10 minutes or less, 9 minutes or less, 8 minutes or less, 7 minutes or less, 6 minutes or less, 5 minutes or less, 4 minutes or less, 3 minutes or less, 2 minutes or less, 90 seconds or less, 75 seconds or less, 60 seconds or less, 45 seconds or less, or 30 seconds or less);
(e) adding an emulsifying oily substance to the mixture before or after incubating in step (d);
(f) centrifuging a mixture obtained in step (e) in a centrifuge having an inner cylinder applied with polypropylene or an inner cylinder equipped with a polypropylene cylinder to obtain a precipitate; and
(g) spraying a substance selected from the group consisting of air, distilled water, saline, and a thickener with a nozzle that is automatically inserted from a top or bottom portion of the cylinder and collecting the precipitate obtained in step (f).

(Drugs)

Examples of drugs used in the present invention include, but are not limited to, nucleic acid molecules that are effective ingredients of a nucleic acid medicament, as well as peptides, polypeptides, and proteins. Examples of nucleic acid medicaments include, but are not limited to, decoys, antisenses, miRNAs, siRNAs, aptamers, and CpG oligos.

An miRNA (microRNA molecule) is generally 20-25 nucleotides in length. An miRNA is processed from a longer precursor RNA molecule ("precursor miRNA") which is called pri-miRNA. A precursor miRNA is transcribed from a non-protein coding gene. A precursor miRNA has two complementary regions enabling the formation of a stem-loop or folding-like structure and is cleaved by an enzyme called Drosha in the nucleus. Drosha is a ribonuclease III-like nuclease. A pre-miRNA produced by cleaving with Drosha is then spliced by an enzyme called a Dicer in the cytoplasm and is taken in by RISC to become an miRNA. An miRNA is typically a part of a stem in a stem-loop of a pri-miRNA.

In the present invention, various nucleic acid medicines (e.g., miRNA) can be used, based on the desired pharmacological effect or physiological effect. For instance, nucleic acid medicines may comprise: a substitution of a hydroxyl group or phosphate group at the 5' end; conversion of phosphodiester bond into another binding format (e.g., phosphothioate bond); and/or glycosylation (e.g., 2'O-Me modification).

Usable miRNAs are not limited. Examples thereof include, but are not limited to,

[miR-34a] 5'-uggcagugucuuagcgguugu-3' (SEQ ID NO: 1),
[miR-148a] 5'-ucagugcacuacagaacuuugu-3' (SEQ ID NO: 2), and
[miR-200a] 5'-uaacacugucugguaacgaugu-3'(SEQ ID NO: 3).

In the present invention, a precursor miRNA or a nucleic acid encoding a precursor miRNA can also be used as an medicament.

(Improvement of Encapsulation Rate)

When the manufacturing method of the present invention is used, the encapsulation rate of a drug (encapsulation rate into carbonate apatite) is drastically better than conventional art. Furthermore, examples of methods of improving the encapsulation rate of a drug include a method of applying a voltage to a solution causing an encapsulation reaction to increase, for example, the probability of a negatively charged drug (e.g., nucleic acid) contacting a positively charged calcium ion, and a method of increasing the probability of a positively charged drug (e.g., anticancer agent) contacting a negatively charged carbonate apatite. However, it is not necessary that a drug has a charge. This is because carbonate apatites and calcium ions have a charge such that they move in a solution by applying a voltage to increase the probability of contacting a drug. Further, an anticancer agent may be negatively charged. This is because the probability of contacting a positively charged calcium ion increases.

The applied voltage is 100 V to 1000 V, but the voltage is not limited thereto. Preferably, the voltage is 200-600 V and more preferably 360-460 V. A voltage is applied for a very short period of time, preferably 1 pulse of 0.6 ms to 1.0 ms is applied 3 to 50 times about every 5 seconds, but voltage application is not limited thereto. A change in the direction (orientation of the + pole and − pole) of application of voltage by 180 degrees each time enables (a) negatively charged drug and a positively charged calcium ion or (b) positively charged drug and a negatively charged carbonate apatite, to move in a mixture solution without a bias to significantly increase the opportunity for contact, resulting in improvement in the encapsulation rate.

(Formulation)

When the aqueous solution of the present invention is used as a medicinal composition/pharmaceutical composition, examples of a carrier contained in the composition include solvents and dispersion media including, but are not limited to, water, ethanol, polyol (e.g., glycerol, propylene glycol, liquid polyethylene glycol and the like), lipids (e.g., triglyceride, vegetable oil, liposome), and combinations thereof. Suitable flowability can be maintained, for example, by using a coating agent such as lecithin, by maintaining the required particle size by dispersion in carriers such as a liquid polyol or lipid, by using a surfactant such as hydroxypropyl cellulose, or a combination of such methods. In many cases, it appears to be preferable to include isotonizing agents such as sugar, sodium chloride or a combination thereof.

The medicinal composition/pharmaceutical composition of the present invention may be formulated with another additional anticancer agent or administered in conjunction with another additional anticancer agent. Although such an anticancer agent is not limited, examples thereof include alkylating agents such as cyclophosphamide hydrate, ifosfamide, thiotepa, busurufan, melphalan, nimustine hydrochloride, ranimustine, dakarupajin, and temozolomide; antimetabolites such as methotrexate, pemetrexed sodium hydrate, fluorouracil, doxifluridine, capecitabine, tagafur, cytarabine, gemcitabine hydrochloride, phosphate ester of fludarabine, nelarabine, cladribine, and levofolinate calcium; antibiotics such as doxorubicin hydrochloride, daunorubicin hydrochloride, pirarubicin, epirubicin hydrochloride, idarubicin hydrochloride, aclarubicin hydrochloride, amrubicin hydrochloride, mitoxantrone hydrochloride, mitomycin C, actinomycin D, bleomycin hydrochloride, peplomycin hydrochloride, zinostatin stimalamer, and calicheamicin; microtubule inhibitors such as vincristine sulfate, vinblastine sulfate, vindesine sulfate, and paclitaxel; aromatase inhibitors such as anastrozole, exemestane, letrozole, and fadrozole hydrochloride hydrate; platinum formulations such as cisplatin, carboplatin, nedaplatin, and oxaliplatin; topoisomerase inhibitors such as irinotecan hydrochloride hydrate, nogitecan hydrochloride, etoposide, and sobuzoxane; adrenocortical steroids such as prednisolone and dexamethasone; thalidomide and its derivatives, lenalidomide; bortezomib which is a protease inhibitor; and the like. These additional anticancer agents may be used independently or as a combination of two or more.

While the present invention is explained hereinafter based on the Examples, the following examples are provided solely for the purpose of exemplification. Thus, the scope of the present invention is not limited by the above-described Detailed Description of the Invention or the following Examples, but solely by the Claims. Although the carbonate apatite of the present invention is not manufacturable only by a specific apparatus, the apparatus shown for example in FIG. 16 can be utilized.

EXAMPLES

Example 1: Effect of Incubation Temperature

In this Example, carbonate apatites were manufactured as discussed below to study the effect of incubation temperatures on particle size.

0.74 g of sodium bicarbonate ($NaHCO_3$) and 180 μL of 1M sodium dihydrogen phosphate dihydrate ($NaH_2PO_4.2H_2O$) were added to 90 ml of distilled water kept cool at 8° C., and distill water was further added such that the total amount would be 100 ml.

The pH of the aqueous solution was adjusted to 7.5 (HCl or NaOH was used).

25 ml each was dispensed into 4 tubes through a 0.22 μm filter.

290 μL of 1M $CaCl_2$ was added to each tube, which was stirred with VOLTEX (about 5-10 seconds).

The tubes were incubated for 30 minutes at 4° C., 8° C., 12° C., 16° C., 20° C., 24° C., 28° C., 32° C., or 37° C.

The particle size distribution (D50, median size) at the time was determined using PARTICA LA960 manufactured by Horiba, Ltd. The measurement values are volume based values. The results are the following.

TABLE 1

| Particle size of carbonate apatites manufactured using various incubation temperatures | |
|---|---|
| Temperature | D50 (median size) |
| 4° C. | 0.381 |
| 8° C. | 0.677 |
| 12° C. | 0.754 |
| 16° C. | 0.887 |
| 20° C. | 2.537 |
| 24° C. | 5.707 |
| 28° C. | 11.042 |
| 32° C. | 14.590 |
| 37° C. | 16.017 |

FIG. 1 shows a more detailed granularity distribution in case of a low temperature (8° C.) or a high temperature (37° C.). The peak for small particle size was higher at a lower temperature (8° C.) than the peak at a high temperature (37° C.). The amount of each reagent was ½ for the sample incubated at a high temperature (37° C.). In view of the above results, it can be understood that an incubation temperature of 10° C. or less is suitable. Although not wishing to be bound by any theory, it is understood that the reason particles become small is incubation at a lower temperature suppresses Brownian motion of particles, resulting in suppression of particle aggregation.

Example 2: Effect of Incubation Time

An experiment similar to Example 1 was conducted. However, the incubation was conducted with an incubation temperature of 8° C. and the times shown in FIG. 2. FIG. 2 shows the results of measurements using PARTICA LA960 manufactured by Horiba, Ltd. In view of the results, it is understood that a shorter incubation time, even at the same low temperature, suppresses secondary aggregate production. Further, FIG. 3A shows an image of carbonate apatite particles produced in incubation at 8° C. for 1 minute, captured with an AFM. The value of Zm indicates an approximate value of the particle diameter. FIG. 3B shows the frequency of particles having each Zm.

Although not wishing to be bound by any theory, when for example the incubation temperature is 8° C., it is understood that a carbonate apatite production reaction is completed in about 1 minute or less and an aggregation reaction is promoted thereafter.

Example 3: Effect of Adding Emulsifying Oily Substance

In this Example, carbonate apatites were manufactured as follows. The results are shown in FIG. 4.
- 0.74 g of sodium bicarbonate ($NaHCO_3$) and 180 μL of 1M sodium dihydrogen phosphate dihydrate ($NaH_2PO_4.2H_2O$) were added to 90 ml of distilled water kept cool at 8° C., and distill water was further added such that the total amount would be 100 ml.
- The pH of the aqueous solution was adjusted to 7.5 (HCl or NaOH was used).
- 25 ml each was dispensed into 4 tubes through a 0.22 μm filter.
- 290 μL of 1M $CaCl_2$ was added to each tube, which was stirred with VOLTEX (about 5-10 seconds).
- The tubes were incubated at 8° C. for 1 minute.
- An emulsifying oily substance (Intralipos) was added such that the concentration was 1% and the mixture was left undisturbed for 10 minutes, 60 minutes, or 24 hours.

All the particles were 700 nm or less, even if the aqueous solution was left undisturbed for up to 24 hours. Although not wishing to be bound by any theory, the results shown in FIG. 4 are understood as an aggregation suppressing effect due to the oiliness of the emulsifying oily substance. However, the aggregation suppressing effect of an emulsifying oily substance is attenuated/eliminated by freezing. Thus, Example 4 was carried out by freezing the solution after discarding the emulsifying oily substance with the supernatant and adding a thickener to the precipitate.

Example 4: Effect of Adding Thickener

In this Example, carbonate apatites were manufactured as follows.
- 0.74 g of sodium bicarbonate ($NaHCO_3$) and 180 μL of 1M sodium dihydrogen phosphate dihydrate ($NaH_2PO_4.2H_2O$) were added to 90 ml of distilled water kept cool at 8° C., and distill water was further added such that the total amount would be 100 ml.
- The pH of the aqueous solution was adjusted to 7.5 (HCl or NaOH was used).
- 25 ml each was dispensed into 4 tubes through a 0.22 μm filter.
- 290 μL of 1M $CaCl_2$ was added to each tube, which was stirred with VOLTEX (about 5-10 seconds).
- The tubes were incubated at 8° C. for 1 minute.
- An emulsifying oily substance (Intralipos) was added such that the concentration was 1%
- The solution was subjected to high-speed centrifugation for 3 minutes at 13,000 G. The emulsifying oily substance was discarded with the supernatant. The precipitate was collected after pipetting by using a thickener (glycerin 40%+glucose 10%) thereon.
- The aqueous solution with carbonate apatites obtained by pipetting dispersed therein was divided into 10 ml each in 50 ml vials and frozen in a −80° C. freezer.
- The vials were placed into a lyophilizer and lyophilized for about 12 hours.
- The vials of powdered carbonate apatite obtained after the lyophilization were stored in the −80° C. freezer.

The results are shown in FIG. 5. All (at least 98% or more) of the particles after lyophilization and dissolution were 700 nm or less. The particle sizes did not change even after the particles were left undisturbed for several hours. Although not wishing to be bound by any theory, the results shown in FIG. 5 are understood to be due to suppression of Brownian motion of particles by the increase in viscosity due to the thickener, resulting in suppression of particle aggregation.

Example 5: Effect of Low Temperature, Short Time Reaction and Addition of Electrophilic Agent on Nucleic Acid Encapsulation Rate FIG. 6 shows the nucleic acid encapsulation rate due to a reaction in incubation at 8° C. for 10 minutes and addition of an electrophilic agent (acetaminophen). An experiment was conducted by using the same conditions as those in Example 2 (7 mg of nucleic acid was used for 115 ml of reaction solution). However, the incubation time of 10 minutes was used to elevate the encapsulation rate of drugs while suppressing all particle sizes to nanometer sizes. The results demonstrate that the encapsulation rate is improved by the addition of an electrophilic agent when a negatively charged drug is to be encapsulated. Although not wishing to be bound by any theory, it is understood that ultrafine particles produced at a low temperature and in a short time first encapsulate a drug (e.g., nucleic acid) at a high rate, and a negatively charged drug (e.g., nucleic acid) that is still free and not encapsulated in the particles is drawn closer by an electrophilic agent to encapsulate almost all drugs (e.g., nucleic acid) in the particles. Similarly, it is understood that the encapsulation ratio is improved by the addition of a nucleophilic agent when a positively charged drug is to be encapsulated.

Example 6: Effect of Application of Voltage on Nucleic Acid Encapsulation Rate

"Without application of voltage" and "With application of voltage" were compared in a low temperature, short time incubation by using the same conditions as the experiment described in Example 5, other than the amount of nucleic acid used being 40 mg. The voltage application conditions were the following: a step of applying one pulse of 0.6-1.0 ms at a voltage of 360-460 V was performed every 5 seconds, which was repeated a total of 50 times. The results are shown in FIG. 7. Although only results of using 40 mg of nucleic acid are shown, similar significant improvement was observed in the nucleic acid encapsulation rate due to voltage application even when the amount of nucleic acid used was higher or lower. The voltage was applied by placing a mixture solution (calcium chloride+nucleic acid) between two parallel electrodes and applying a voltage. Between the electrodes, a current flows as in a homogeneous layer. Although not wishing to be bound by any theory, it is understood that a negatively charged nucleic acid moves to the positive electrode side and the positively charged calcium ion moves to the negative electrode side to dramatically improve the opportunity of contact of the nucleic acid and calcium ion when a current flows, resulting in an improved nucleic acid encapsulation rate of carbonate apatites.

It is understood to be more preferable to apply a voltage multiple times and to reverse the direction of the current each time. The reason therefor is understood to be further increase in the opportunity of contact because of a nucleic acid and calcium ion moving in opposite directions each time.

Example 7: Antitumor Cell Experiment Using Human Lung Cancer Cell Line with Nucleic Acid Encapsulating Carbonate Apatite of the Present Invention In this Example, a cell experiment was conducted with nucleic acid encapsulating carbonate apatites as follows. The antitumor effects were compared between low temperature, short time incubation of the present invention and high temperature, long time incubation of conventional art.

(Cells)

This Example used the A549 cell line (adenocarcinomic human alveolar basal epithelial cell line), but the cell line is not limited thereto. For instance, as is apparent from the results in Example 8, cell lines other than the A549 cell line, such as HCT116 (human colonic adenocarcinoma cell line), MIA PaCa-2 (human pancreatic adenocarcinoma cell line), Hep-G2 (human liver cancer cell line), OCUB-M (human breast cancer cell line), HeLa (human cervical cancer cell line), SH-10-TC (human gastric cancer cell line), NIH: OVCAR-3 (human ovarian cancer cell line), or the like may also be used. A 6-well plate was used, while 10% FBS-DMEM was used as the medium, to seed $2.0\times10^5$ cells/well. (1) Negative control (NC) without transfection; (2) miR-negative control (miR-NC) encapsulating carbonate apatite; (3) Carbonate apatite that is not encapsulating a nucleic acid (8° C. 10 minutes and 37° C. 30 minutes); and (4) Nucleic acid encapsulating carbonate apatite (3.0 µg/well) (8° C. 10 minutes and 37° C. 30 minutes). The number of samples was n=3 in each case. They were measured at each of 24 hours, 48 hours, and 72 hours.

(Nucleic Acid)

This Example used miR-34a (5'-uggcagugucuuagcug-guugu-3'(SEQ ID NO: 1)), but the nucleic acid is not limited thereof. For example, miR-148a 5'-ucagugcacuacagaac-uuugu-3' (SEQ ID NO: 2)), miR-200a (5'-uaacacugucug-guaacgaugu-3' (SEQ ID NO: 3)), or the like may also be used. Further, a combination thereof may also be appropriately used.

(Low Temperature, Short Time Incubation)

0.74 g of sodium bicarbonate ($NaHCO_3$) and 180 µL of 1M sodium dihydrogen phosphate dihydrate ($NaH_2PO_4.2H_2O$) were added to 90 ml of distilled water kept cool at 8° C., and distill water was further added such that the total amount would be 100 ml.

The pH of the aqueous solution was adjusted to 7.5 (HCl or NaOH was used).

20 ml each was dispensed into 3 tubes of 25 ml tube through a 0.22 µm filter.

30 µg of miR-34a was added to the first tube and lightly stirred. 30 µg of miR-NC (negative control) (RNAi Inc. Banno Negacon) was added to the second tube and lightly stirred. Nothing was added to the third tube (negative control (NC)).

232 µL of 1M $CaCl_2$ was added to the 20 ml mixture, which was stirred with VOLTEX (about 5-10 seconds).

The tubes were incubated at 8° C. for 10 minutes.

All samples with processed by the following high temperature, long time incubation and common protocol.

(High Temperature, Long Time Incubation)

0.37 g of sodium bicarbonate ($NaHCO_3$) and 90 µL of 1M sodium dihydrogen phosphate dihydrate ($NaH_2PO_4.2H_2O$) and 180 µL of 1M calcium chloride ($CaCl_2$) were added to 90 ml of distilled water at room temperature, and distill water was further added such that the total amount would be 100 ml.

The pH of the aqueous solution was adjusted to 7.5 (HCl or NaOH was used).

20 ml each was dispensed into 2 tubes of 25 ml tube through a 0.22 µm filter.

30 µg of miR-34a was added to the first tube and lightly stirred. Nothing was added to the second tube.

80 µL of 1M $CaCl_2$ was added to the 20 ml mixture, which was stirred with VOLTEX (about 5-10 seconds).

The tubes were incubated at 37° C. for 30 minutes.

The following common protocol was then conducted.

(Common Protocol)

Total of 5 tubes described above were subjected to high-speed centrifugation for 3 minutes at 13,000 G at 4° C. and the supernatant was discarded. The precipitate was collected after pipetting 20 ml of 10% FBS-DMEM thereon.

2 ml was seeded per well for transfection. The amount of addition of miR-34a per well was 3.0 µg.

The wells were cultured within an incubator of 37° C./5% $CO_2$ concentration.

The number of cells was counted at 24 hours, 48 hours, and 72 hours. COUNTESS II FL was used for the measurements.

The results are shown in FIG. 8. The squares "☐" indicate the results of the negative control (NC) without transfection. Xs "x" indicate miR-negative control ("miR-NC", molecules without miRNA activity) encapsulating carbonate apatites. Incubation was carried out for 10 minutes at 8° C. Triangles "Δ" indicate results of adding to each well 3.0 µg of carbonate apatites encapsulating the nucleic acid miR-34a, which was manufactured by incubation at 37° C. for 30 minutes. Circles "●" indicate results of adding to each well 3.0 µg of carbonate apatites encapsulating the nucleic acid miR-34a, which was manufactured by incubation at 8° C. for 10 minutes, and measuring the live cell count after 24 hours, 48 hours and 72 hours. The number of samples was n=3 for each case. Despite the amount of added nucleic acid being the same, the antitumor effect was significant in the low temperature, short time incubation. Although not wishing to be bound by any theory, it is understood that this is because the low temperature, short time incubation produced many ultrafine particles and improved the nucleic acid encapsulation rate, and the efficiency of transfection into cells also improved due to the particle size being small. Although not shown in FIG. 8, there is no difference in the results between carbonate apatites that are not encapsulating a nucleic acid and negative controls such as miR-NC encapsulating carbonate apatite or NC. Thus, it is understood that the carbonate apatite itself does not have any antitumor effect.

Example 8: Antitumor Cell Experiment Using Human Colonic Adenocarcinoma Cell Line Due to the Nucleic Acid Encapsulating Carbonate Apatite of the Present Invention An experiment similar to Example 7 was conducted on human colonic adenocarcinoma cell line, i.e., HCT116 cell line, to test the growth suppression effect on tumor cells.

Specifically, a 6-well plate was used, while 10% FBS containing DMEM was used as the medium, to seed $1.2 \times 10^5$ cells/well. 3.0 µg of carbonate apatite encapsulating various nucleic acids was added to each well to test the growth suppression effect on tumor cells. The results are shown in FIG. 9. The symbols in the figure are the same as in FIG. 8.

Results similar to the results in Example 7 were obtained. That is, despite the amount of added nucleic acid being the same, the antitumor effect was significant in the low temperature, short time incubation. Although not wishing to be bound by any theory, it is understood that this is because the low temperature, short time incubation produced many ultrafine particles and improved the nucleic acid encapsulation rate, and the efficiency of transfection into cells also improved due to the particle size being small. Although not shown in FIG. 9, when experiments were conducted on negative controls made by using various different incubation temperatures for the carbonate apatite that is not encapsulating a nucleic acid, there is no difference in the results from negative controls such as miR-NC encapsulating carbonate apatites or NC regardless of the incubation temperature. Thus, it is understood that the carbonate apatite itself does not have any antitumor effect.

The antitumor effect was similarly significant in the low temperature, short time incubation even in antitumor cell experiments using other cancer cell lines (data not shown).

Example 9: Antitumor Cell Experiment Using Human Colonic Adenocarcinoma Cell Strain when Using Nucleic Acids Applied with Voltage In order to verify that the antitumor effect of nucleic acids applied with a voltage does not change in quality, an experiment was conducted that is similar to the experiment described in Example 8 on the human colonic adenocarcinoma cell line, i.e., HCT116 cell line, to test the growth suppression effect on tumor cells. miR-34a was used as the nucleic acids, and voltages were applied for 50 times on the mixture solution of the nucleic acid and calcium chloride in about a 5 second interval at 360-460 V. $2.0 \times 10^5$ cells/well were seeded. 3.0 µg of each of carbonate apatites encapsulating a nucleic acid prepared by applying a voltage and carbonate apatites encapsulating a nucleic acid prepared without applying a voltage were added to each well to test the growth suppression effect on tumor cells. The results are shown in FIG. 10. The squares "□" indicate the results of the negative control (NC) without transfection. Triangles "Δ" indicate results of adding to each well 3.0 µg of carbonate apatites encapsulating the nucleic acid miR-34a, which was manufactured by incubation at 8° C. for 10 minutes without applying a voltage. Circles "●" indicate results of adding to each well 3.0 µg of carbonate apatites encapsulating the nucleic acid miR-34a, which was manufactured by incubation at 8° C. for 10 minutes while applying a voltage, and measuring the live cell count after 24 hours, 48 hours and 72 hours.

From the results of FIG. 10, it was verified that nucleic acids applied with a voltage had not lost the tumor suppression effect and had the same function as nucleic acids that were not applied with a voltage.

Example 10: Antitumor Effect Experiment Using Cancer Carrying Nude Mice

An antitumor effect experiment using cancer carrying nude mice was conducted. The following is the summary of the experimental procedure.

(1. Experiment with a Model Mouse Made by Using Human Gastric Cell Line)
(1.1. Preparation of Carbonate Apatite Solution)
A carbonate apatite solution was prepared as follows.
A buffer solution comprising 0.74 g of $NaHCO_3$ and 180 µL 1M $NaH_2PO_4 \cdot 2H_2O$ in a solution adjusted to 100 ml with distilled water kept cool at 8° C. was prepared. The pH of the buffer solution was adjusted to 7.5, and the buffer solution was filtered and sterilized with a 0.22 µm filter.
0.644 ml of the above-described buffer solution was dispensed into tubes. 28 µg of miR-34a nucleic acid and then 7.47 µl of 1M $CaCl_2$ were added to each tube. The mixture was incubated at 8° C. for 10 minutes and centrifuged at 13,000 G for 3 minutes. The supernatant was discarded.
The precipitate of each tube was dissolved in 0.7 ml of saline to prepare a miR-148a 28 µg/0.7 ml solution, which was immediately cooled with ice.
0.1 ml of the solution comprising 4 µg of nucleic acid is used for administration per one mouse.

(1.2. Preparation of Cancer Carrying Nude Mouse)
Cancer carrying model nude mice in which the SH-10-TC (human gastric cancer) cell line was transplanted subcutaneously on the back of a 7 weeks old female nude mouse (BALB/c·Slc·nu/nu) were used. On the day the average tumor volume exceeded 80 mm³, mice were grouped into 6 mice (n=6) for each group such that the difference in the average tumor volume was as small as possible among each group. Carbonate apatites were administered 7 times every other day for 14 days. The change in the average tumor volume in each group was recorded.

(1.3. Results)
FIG. 11 shows the results of measuring the tumor volume on the day of transplantation, and 4 days, 8 days, 11 days, and 14 days after the transplantation (average value±standard error). Diamonds "♦" indicate results for mice injected with saline in the caudal vein. White squares "□" indicate the results for mice injected with the negative control miR-NC in the caudal vein. Black squares "■" indicate the results for mice injected with miR-148a in the caudal vein. "*" indicates when the miR-148a group has a significant difference at p<0.05 from the miR-NC group.

(2. Experiment with a Model Mouse Made by Using Human Colonic Adenocarcinoma Cell Line)
Other than using the above-described human colonic adenocarcinoma cell line (HCT116), the same experiment as the above-described "1. Experiment with a model mouse made by using human gastric cell line" was conducted. miR-34a was used as nucleic acid molecules. "" indicates that the miR-34a group has a significant difference at p<0.01 from the miR-NC group. The results are shown in FIG. 12. The symbols in the figure are the same as in FIG. 11**. However, black squares "●" indicate results for mice injected with miR-34a in the caudal vein.

(3. Discussion)
In model mice using either the human gastric cell line or the human colonic adenocarcinoma cell line, significant suppression of increase in the average tumor volume was confirmed in groups administered with nucleic acid encapsulating carbonate apatites.

Example 11: Test for Intravenous Administration of Nucleic Acid Encapsulating Carbonate Apatite Using Cynomolgus Monkey The expected human dose of nucleic acid encapsulating carbonate apatite converted by the body weight of a cynomolgus monkey was administered once per day consecutively for 10 days to study the safety thereof. Specifically, when a single dose of miRNA is assumed to be 10 mg when the body weight of a human is 50 kg, a dose to one cynomolgus monkey of 0.6 mg was determined to be the normal dose when the body weight of a cynomolgus monkey is for example 3 kg. In this test, safety was studied by administrating double the amount (1.2 mg for 3 kg) for each dose. A single dose was determined to be 1.2 mg (male: 0.24 mg/kg, female: 0.40 mg/kg) as the nucleic acid (miR-34a) amount.

The following is the preparation protocol for the administered nucleic acid encapsulating carbonate apatite.

A buffer solution comprising 0.204 g of NaHCO$_3$ and 49.68 μL of 1M NaH$_2$PO$_4$.2H$_2$O in a solution adjusted to 27.6 ml with distilled water kept cool at 8° C. was prepared. The pH of the buffer solution was adjusted to 7.5, and the buffer solution was then filtered and sterilized with a 0.22 μm filter.

1200 μg of miR-34a nucleic acid and then 320.2 μl of 1M CaCl$_2$ were added.

The mixture was incubated at 8° C. for 1 minute and 1.394 ml of 20% Intralipos was added (final concentration of 1%). The mixture was further incubated at 8° C. for 10 minutes and centrifuged at 13,000 G for 3 minutes at 4° C. The supernatant was discarded.

1.656 ml of 50% glycerin (concentration 30%) and 1.104 ml of 50% glucose (concentration 20%) were added to the precipitate of each tube, which was dissolved to prepare a miR-34a 1200 μg/1.38 ml solution. The solution was diluted 1.5-fold for use with saline immediately prior to use (glycerin final concentration of 20% and glucose final concentration of 13.3%).

As a result, a change suggesting an effect due to nucleic acid encapsulating carbonate apatite administration was not observed on the general condition, body weight, amount of feeding, urine test, or blood chemical analysis. In view of the above, it was confirmed that the nucleic acid and carbonate apatite used are not toxic to the living body nor cause intravascular embolism or the like.

In addition, it was confirmed that no abnormality was observed in cynomolgus monkeys in all intravenous administration tests including an intravenous repeat administration test that administered each of miR-34a, miR-148a, and miR-200a 7 times every other day for 14 days, intravenous single administration test that used oxaliplatin and cisplatin, and two other experimental systems.

Example 12: Clinical Trial (1. Preparation of Nucleic Acid Encapsulation Carbonate Apatite for Clinical Trial)

A buffer solution comprising 2.553 g of NaHCO$_3$ and 621 μL of 1M NaH$_2$PO$_4$.2H$_2$O in a solution adjusted to 115 ml with distilled water (for injection) kept cool at 4° C. was prepared. The pH of the buffer solution was adjusted to 7.5, and the buffer solution was filtered and sterilized with a 0.22 μm filter. 28.75 ml each of the resulting solution was dispensed into 4 tubes.

3.75 mg of nucleic acid, and then 1000.5 μl of 1M CaCl$_2$ were added to each tube.

1.513 ml of 20% Intralipos was added (final concentration of 1%). The mixture was incubated at 4° C. for 10 minutes and centrifuged at 9,100 G for 5 minutes at 4° C. The supernatant was discarded.

9.0 ml of 50% glycerin (final concentration 30%) and 6.0 ml of 50% glucose (final concentration 20%) were added to the precipitate in the four tubes, which was dissolved, placed into vial with a capacity of 30 ml, frozen and stored (15 mg of nucleic acid, 15 ml of solution per vial).

(2. Clinical Trial Targeting a 63 Years Old Male with Colon Cancer and Multiple Liver Metastasis)

15 mg/day of miR-148a was administered by intravenous instillation of carbonate apatites encapsulating miR-148a as the drug (15 ml of carbonate apatite solution+100 ml of saline). Once daily administration administered for 10 consecutive days was considered 1 course. A single administration time was 30 minutes. A single dose of miRNA was determined from the total volume of tumor of the patient based on CT image.

FIG. 13 shows the results of CT before and after the therapy. The CT examination confirmed the elimination of metastatic lesion in the liver (encircled portions). In view of the above, it is confirmed that nucleic acid encapsulating carbonate apatites are effectively delivered to cancer tissues without being captured or processed by the reticuloendothelial system, and are very effective as a cancer therapeutic drug. Further, since there was no side effect, it was confirmed that nucleic acid encapsulating carbonate apatites are delivered to cancer tissues without being destroyed in the circulating blood and release nucleic acids after phagocytosis into a cancer cell.

(3. Clinical Trial Targeting a 76 Years Old Male with Pancreatic Cancer)

15 mg/day of miR-34a was administered by intravenous instillation of carbonate apatites encapsulating miR-34 as the drug (15 ml of carbonate apatite solution+100 ml of saline). Once daily administration administered for 10 consecutive days was considered 1 course. A single administration time was 30 minutes.

FIG. 14 shows the results of CT before and after therapy. CT examination confirmed dramatic contraction in the primary lesions on the pancreatic body (encircled portions). Pancreatic cancer is already inoperable upon the discovery of the cancer in many cases. It is also a type of cancer on which an anticancer agent is very ineffective. Thus, the results of this trial demonstrate that nucleic acid encapsulating carbonate apatites can be a very effective therapeutic drug against pancreatic cancer.

(4. Preparation of Anticancer Agent Encapsulating Carbonate Apatite for Clinical Trial)

Other than the drug being 64 mg of oxaliplatin, anticancer agent encapsulating carbonate apatites were prepared by the same method as in the aforementioned "1. Preparation of nucleic acid encapsulation carbonate apatite for clinical trial".

(5. Clinical Trial Targeting a 55 Years Old Male with Esophageal Cancer and Multiple Lung Metastasis)

64 mg/day of oxaliplatin was administered by intravenous instillation of carbonate apatites encapsulating oxaliplatin as the anticancer agent (15 ml of carbonate apatite solution+ 100 ml of saline). Once weekly administration administered for 8 consecutive weeks was considered 1 course. A single administration time was 60 minutes. A single dose of anticancer agent was determined from the body surface area of the patient. A single dose of carbonate apatite was determined in the range where the amount of calcium contained in carbonate apatites does not exceed the upper limit amount/day for adults in a Calcicol injection (8.5%).

FIG. 15 shows the results of CT before and after the therapy. CT examination confirmed the elimination of lung metastatic lesions (encircled portions). The result demonstrates that the carbonate apatite of the present invention is notably excellent not only for a nucleic acid such as miRNA, but also for anticancer agent administration.

The effects are confirmed in many cases other than those discussed above.

INDUSTRIAL APPLICABILITY

The method of manufacturing a carbonate apatite in the present invention can precisely control the particle size (average particle size, variance of particle sizes, and maximum particle size) by incubation temperature and incubation time. As a result, it is possible to manufacture carbonate apatites suitable for delivery of a drug into cell and/or tissue. With the present invention, it is understood that carbonate apatites with a high drug encapsulating rate, maximum particle size of 700 nm or less, and average particle size of 30 nm or less, all in nanometer size are used for focused delivery of a selective therapeutic gene, anticancer agent or the like according to the residual cancer in the late stage cancer patient, such that therapy without burden on the body but with a high antitumor effect would dramatically develop.

population of carbonate apatites have a particle size of 700 nm or less, and (ii) average particle size of the population of carbonate apatites is 50 nm or less.

2. The method of claim 1, wherein the mixture further comprises an emulsifying oily substance.

3. The method of claim 1, wherein 90% or more of the population of carbonate apatites have a particle size of 700 nm or less.

4. The method of claim 1, wherein the average particle size of the population of carbonate apatites is 50 nm or less.

5. A method of preparing an aqueous dispersion comprising a population of carbonate apatites which comprise a drug encapsulated therein, comprising the steps of:
(a) incubating, without treating with ultrasound waves, a mixture comprising a calcium ion, a phosphate ion, a hydrogen carbonate ion, and a drug at an incubation temperature of 1° C. to 8° C. and an incubation time of 1 minute or less, to produce in the mixture a population of carbonate apatites encapsulating the drug;
(b) subjecting the mixture after completion of incubation to high-speed centrifugation to produce a precipitate

The invention claimed is:

1. A method of manufacturing a carbonate apatite encapsulating a drug, the method comprising the step of incubating, without treating with ultrasound waves, a mixture comprising a calcium ion, a phosphate ion, a hydrogen carbonate ion, and a drug at an incubation temperature of 1° C. to 8° C. and an incubation time of 1 minute or less to obtain a population of carbonate apatites encapsulating the drug, and wherein at least one of: (i) 90% or more of the which comprises the population of carbonate apatites encapsulating the drug; and (c) dispersing the precipitate produced in step (b) in an aqueous solution to obtain the aqueous dispersion, and wherein at least one of: (i) 90% or more of the population of carbonate apatites have a particle size of 700 nm or less, and (ii) average particle size of the population of carbonate apatites is 50 nm or less.

6. The method of claim 5, wherein the mixture further comprises an emulsifying oily substance.

7. The method of claim 5, wherein a voltage is applied to the mixture while the mixture is incubating.

8. The method of claim 5, wherein 90% or more of the population of carbonate apatites have a particle size of 700 nm or less.

9. The method of claim 5, wherein the average particle size of the population of carbonate apatites is 50 nm or less.

10. A method of manufacturing a carbonate apatite encapsulating a drug, comprising the steps of:
   (a) loading water, which is manufactured by an RO water manufacturing apparatus or by a distilled water manufacturing apparatus, into a container for stirring;
   (b) loading a phosphate ion and a hydrogen carbonate ion into the water of step (a) to produce a mixture;
   (c) adjusting pH of the mixture produced in step (b) to a pH value of 6.0 to 9.0, to obtain a pH-adjusted mixture;
   (d) loading a calcium ion and a drug into the pH-adjusted mixture obtained in step (c) and incubating the mixture at a temperature of 1° C. to 8° C. for 1 minute or less;
   (e) adding an emulsifying oily substance to the pH-adjusted mixture obtained in step (c) before or after said incubating in step (d);
   (f) centrifuging the pH-adjusted mixture to which the emulsifying oily substance has been added in step (e) in a centrifuge and discarding a supernatant to obtain a precipitate that comprises a population of carbonate apatites comprising the carbonate apatite-encapsulated drug; and
   (g) dispersing, without treating with ultrasound waves, the precipitate obtained in step (f) in a substance selected from air, distilled water, saline, and a thickener to obtain a dispersion comprising the population of carbonate apatites, and therefrom collecting the carbonate apatite-encapsulated drug, and wherein at least one of: (i) 90% or more of the population of carbonate apatites have a particle size of 700 nm or less, and (ii) average particle size of the population of carbonate apatites is 50 nm or less.

11. The method of claim 10, further comprising the step of:
   (h) bottling and lyophilizing the carbonate apatite-encapsulated drug collected in step (g).

12. The method of claim 10, wherein 90% or more of the population of carbonate apatites have a particle size of 700 nm or less.

13. The method of claim 10, wherein the average particle size of the population of carbonate apatites is 50 nm or less.

* * * * *